United States Patent
Chretien et al.

(10) Patent No.: US 11,013,830 B2
(45) Date of Patent: May 25, 2021

(54) 5-HYDROXYTRYPTAMINE 1B RECEPTOR-STIMULATING AGENT FOR ENHANCING IN VIVO ENGRAFTMENT POTENTIAL

(71) Applicants: INSTITUT PASTEUR, Paris (FR); UNIVERSITE PARIS DESCARTES, Paris (FR); CENTRE HOSPITALIER SAINTE ANNE PARIS, Paris (FR)

(72) Inventors: Fabrice Bruno Chretien, Paris (FR); Raphael Gaillard, Paris (FR); Pierre Rocheteau, Paris (FR)

(73) Assignees: INSTITUT PASTEUR, Paris (FR); UNIVERSITE PARIS DESCARTES, Paris (FR); CENTRE HOSPITALIER SAINTE ANNE PARIS, Paris (FR)

( * ) Notice: Subject to any disclaimer, the term of this patent is extended or adjusted under 35 U.S.C. 154(b) by 0 days.

(21) Appl. No.: 15/776,769

(22) PCT Filed: Jun. 15, 2016

(86) PCT No.: PCT/EP2016/066965
§ 371 (c)(1),
(2) Date: May 16, 2018

(87) PCT Pub. No.: WO2017/084774
PCT Pub. Date: May 26, 2017

(65) Prior Publication Data
US 2018/0326121 A1    Nov. 15, 2018

Related U.S. Application Data

(60) Provisional application No. 62/257,816, filed on Nov. 20, 2015.

(30) Foreign Application Priority Data

Apr. 15, 2016   (EP) .................................. 16305446

(51) Int. Cl.
| | | |
|---|---|---|
| *A61K 31/495* | (2006.01) | |
| *A61L 27/36* | (2006.01) | |
| *A61K 35/12* | (2015.01) | |
| *A61K 31/138* | (2006.01) | |
| *A61K 31/496* | (2006.01) | |
| *A61K 31/499* | (2006.01) | |
| *A61K 31/675* | (2006.01) | |
| *A61L 27/54* | (2006.01) | |

(52) U.S. Cl.
CPC ........ *A61L 27/3687* (2013.01); *A61K 31/138* (2013.01); *A61K 31/495* (2013.01); *A61K 31/496* (2013.01); *A61K 31/499* (2013.01); *A61K 31/675* (2013.01); *A61K 35/12* (2013.01); *A61L 27/54* (2013.01); *A61L 2430/02* (2013.01); *A61L 2430/30* (2013.01)

(58) Field of Classification Search
None
See application file for complete search history.

(56) References Cited

U.S. PATENT DOCUMENTS

| | | |
|---|---|---|
| 10,493,046 B2 | 12/2019 | Chretien et al. |
| 2018/0303772 A1 | 10/2018 | Chretien et al. |
| 2019/0290641 A1 | 9/2019 | Gaillard et al. |
| 2020/0060999 A1 | 2/2020 | Chretien et al. |

FOREIGN PATENT DOCUMENTS

| | | | | |
|---|---|---|---|---|
| WO | 03/029232 A1 | 4/2003 | | |
| WO | WO-03029232 A1 * | 4/2003 | ......... | C07D 295/096 |
| WO | 2007/44005 A1 | 12/2007 | | |
| WO | 2007/148341 A2 | 12/2007 | | |
| WO | 2008/078353 A1 | 7/2008 | | |
| WO | 2010/125348 A1 | 11/2010 | | |
| WO | 2012/174537 A2 | 12/2012 | | |
| WO | 2013/076245 A1 | 5/2013 | | |
| WO | WO-2013076245 A1 * | 5/2013 | ............. | A61K 45/06 |
| WO | 2014/190063 A1 | 11/2014 | | |
| WO | 2017/013031 A1 | 1/2017 | | |
| WO | 2017/063771 A1 | 4/2017 | | |
| WO | 2017/084774 A1 | 5/2017 | | |
| WO | 2018/011382 A1 | 1/2018 | | |

OTHER PUBLICATIONS

Pauwels, 1994, "The 5-HT1D Receptor antagonist GR127,935 is an agonist at Cloned Human 5-HT1Dα Receptor sites," Neuropharmacology, vol. 34, No. 2, pp. 235-237 (1995).
Sauer, 2003, "Effect of antidepressants and their relative affinity for the Serotonin Transporter on the Risk of Myocardial Infarction.," Circulation, vol. 108, pp. 32-36.
Jiang, 2004, "Should SSRI be prescribed to all Patients with Ischemic Heart Disease?" Current Psychiatry Reports, Current Science, vol. 6, pp. 202-209.
Malick, 2014, "Desvenlafaxine reduces apoptosis in amygdala after myocardial infarction," Brain Research Bulletin, vol. 109, pp. 158-163.
Droggrell, 2003, "The role of 5-HT on the cardivascular and renal systems and the clinical potential of 5-HT modulation," Expert Opin. INvestig. Drugs, vol. 12, pp. 805-823.
Husamettin, 2002, "Amplification of sumatriptan-induced contractions with phenylephrine, histamine and KCl in the isolated human mesenteric artery: in vitro evidence for sumatriptan-induced mesenteric ischaemia," Naunyn-Schmiedeberg's Arch Pharmacol, vol. 366, pp. 254-261.
Malinin, 2003, "Treatment with selective serotonin reuptake inhibitors for enhancing wound healing," Medical Hypotheses, vol. 63, pp. 103-109.

(Continued)

*Primary Examiner* — Heidi Reese
(74) *Attorney, Agent, or Firm* — Arrigo, Lee, Guttman & Mouta-Bellum LLP

(57) ABSTRACT

The present invention relates to the field of regenerative medicine, and more particularly to the improvement of the in vivo engraftment potential of biological material to be administered to a subject in need thereof.

11 Claims, 5 Drawing Sheets

(56) References Cited

OTHER PUBLICATIONS

Nguyen, (Abstract) 2016, "Serotonin as a potential therapeutic target for mesenchymal stem cell—Mediated improvement of wound healing," Journal of Investigative Dermatology, S133.
Connie Sanchez, et al., "Vortioxetine, a novel antidepressant with multimodal activity: Review of preclinical and clinical data," Pharmacology & Therapeutics, vol. 145 (2015), pp. 43-57.
Asres Berhan and Alex Barker, "Vortioxetine in the treatment of adult patients with major depressive disorder: a meta-analysis of randomized double-blind controlled trials," BMC Psychiatry 2014, 14:276.

\* cited by examiner

5-HYDROXYTRYPTAMINE 1B RECEPTOR-STIMULATING AGENT FOR ENHANCING IN VIVO ENGRAFTMENT POTENTIAL

INTRODUCTION

The present invention relates to the field of regenerative medicine, and more particularly to the improvement of the in vivo engraftment potential of biological material to be administered to a subject in need thereof.

Cell-based therapies for the prevention and treatment of several organs dysfunctions offer the potential to significantly modulate the function and outcomes in patients in the treatment and cures of a wide variety of pathological disorders. To date, several clinical studies have suggested the potential efficacy of various cell types, in particular stem cells (Rennert et al., 2012; Perin et al., 2013; Meng et al., 2015; Liu et al., 2015). However, the benefits observed so far in clinical trials have been inconsistent and modest.

In parallel, preclinical studies have identified key events in the process of cell-based repair, including stem cell homing, engraftment, survival, paracrine factor release, and differentiation that need to be optimized to maximize repair and function (Rennert et al., 2012).

These observations highlight the need in the art to develop new drugs that can prepare the biological material to be administered (either in the form of cells, tissue and/or organ), and/or prime the subject to receive said biological material so as to optimize these key events in the hope of maximizing clinical benefit for the patient.

The present invention addresses the above discussed need in the art.

In particular, the inventors have surprisingly and unexpectedly discovered that fluoxetine and vortioxetine display pro-engraftment capacities. Indeed, their in vivo administration to mice prior to cell grafting, and continued thereafter, led, post-graft, to an increase in the number of grafted myogenic and hematopoietic stem cells in the skeletal muscle and bone marrow, respectively. Similar observations, albeit with a slightly lower increase in the number of grafted cells, were made when mice were administered said agents only after cell grafting. The present results thus demonstrate that these antidepressant agents can enhance engraftment potential of various types of biological material, and hence be used as a pre-treatment, co-treatment and/or post-treatment of cell therapies, tissues grafts or organ transplants. To do so, one can either choose to contact, in vitro or ex vivo, the biological material to be administered to the patient with said antidepressant agent(s), and/or directly administer in vivo said agent(s) to the patient, prior to, during or after regenerative therapy. The antidepressant agent may also be administered to the donor of the biological material. The inventors further observed that the duration of the in vivo pre-treatment was much shorter with vortioxetine than with fluoxetine (12 days versus 6 weeks in mice, respectively), in order to achieve the same increase in stem cell count after cell graft: these data further highlight the importance of vortioxetine in regenerative medical applications as proposed herein, due to the rapidity of onset of its beneficial effects on in vivo engraftment potential. Finally, the inventors identified that fluoxetine and vortioxetine promote pro-engraftment, via 5-hydroxytryptamine 1B receptor stimulation. Altogether, these results suggest that the in vivo potential engraftment is enhanced through the stimulation of the 5-hydroxytryptamine 1B receptor.

Accordingly, the present invention relates to methods for enhancing the in vivo engraftment potential of biological material relying on the use of an agent stimulating the 5-hydroxytryptamine 1B receptor. It further encompasses the biological material obtainable by said methods, a medical device comprising said biological material, and therapeutic methods using said biological material or said medical device and/or an agent stimulating the 5-hydroxytryptamine 1B receptor in a subject in need thereof.

DETAILED DESCRIPTION OF THE INVENTION

Unless stated otherwise, scientific and technical terms used in connection with the present invention shall have the meanings that are commonly understood by those of ordinary skill in the art. Furthermore, unless otherwise required by context, nomenclatures used herein, and techniques of molecular biology, cell culture, and pharmacology are those well-known and commonly used in the art. Such techniques are fully explained in the literature (see Ausubel et al., Current Protocols in Molecular Biology, Eds., John Wiley & Sons, Inc. New York, 2013; Remington: The Science and Practice of Pharmacy, 22nd ed., Mack Publishing Co., Easton, Pa., 2012).

Definitions are provided throughout the specification.

Methods and Products According to the Invention

As indicated above, the inventors have discovered that the administration of fluoxetine or vortioxetine, two agents stimulating the 5-hydroxytryptamine 1B receptor (5-HT1 BR), indirectly (through increased serotonin levels for fluoxetine and vortioxetine) and/or directly (through 5-HT1 BR partial agonism for vortioxetine), greatly enhance the in vivo engraftment potential of biological material that is to be grafted in a subject in need thereof. This discovery paves the way to new and innovative applications in regenerative medicine, which are detailed below.

The present invention therefore proposes a first method, which consists in contacting an isolated biological material with a 5-hydroxytryptamine 1B receptor (5-HT1 BR)-stimulating agent prior to the administration of said material—by way of cell therapy, tissue graft or organ transplant—to a subject in need thereof.

Accordingly, in a first aspect, the present invention is directed to a method for enhancing the in vivo engraftment potential of a biological material, comprising at least, or consisting essentially of, or consisting of the step of in vitro and/or ex vivo contacting an isolated biological material with at least one 5-hydroxytryptamine 1B receptor (5-HT1 BR)-stimulating agent.

In other words, the present invention is preferably directed to a method for enhancing the in vivo engraftment potential of a biological material, comprising, or consisting essentially of, or consisting of the following steps:
 a) optionally, obtaining a biological material;
 b) in vitro and/or ex vivo contacting said isolated biological material with at least one 5-hydroxytryptamine 1B receptor (5-HT1 BR)-stimulating agent; and
 c) optionally, recovering said biological material.

According to a preferred embodiment, the above method is solely performed on an isolated biological material (and therefore does not comprise the above step a)), and as such is conducted only in vitro and/or ex vivo. Said method can thus be performed prior to a treatment intended to administer the biological material to a subject in need thereof.

According to a preferred embodiment, an effective amount of 5-HT1 BR-stimulating agent is used in the above method. By "effective amount", it is meant herein that the agent of the invention is contacted (or incubated) with said biological material in a quantity sufficient to provide the effect for which it is indicated, i.e. enhancement of the in vivo engraftment potential of said biological material.

Yet, according to a preferred embodiment, the above in vitro or ex vivo contacting step is performed for an effective period of time. By "effective period of time", it is meant herein that the isolated biological material and the 5-HT1 BR-stimulating agent are contacted (or incubated with each other) for a period of time sufficient to provide the effect for which it is indicated, i.e. enhancement of the in vivo engraftment potential of said biological material.

Preferably, said effective period of time is comprised between about 5 hours to about 40 days, preferably between about 0.5 days to about 35 days, between about 5 days to about 30 days, more preferably between about 5 hours to about 5 days, even more preferably for about 2 days.

By "in vivo engraftment potential" of a biological material, it is meant herein the in vivo expansion and/or homing of cells originating from a biological material after administration of said material to a subject in need thereof (i.e. recipient). In other words, it refers herein to the growth of newly formed cells (such as stem cells and/or differentiated cells) from said biological material and/or the establishment of residence of said newly formed cells within the recipient after administration of said material to said recipient. Whether the biological material is made of cells, tissues or organs as further described below, the engraftment potential of said material can be assessed by measuring the number of cells from a biopsy of the administered biological material, and by comparing said number to a value of reference. For example, in the context of the present invention, the value of reference can be the number of cells from a biopsy of an administered biological material that has not been contacted with a 5-HT1 BR-stimulating agent. Alternatively, the in vivo potential of engraftment can be said to be enhanced, when the number of cells from the biological material, such as stem cells and/or differentiated cells, is increased after administration of said material to the subject. Indeed, as illustrated in the examples, the percentage or area of the tissue that was reconstituted from the donor cells was higher after grafting cells. In other words, the potential of engraftment is said to be enhanced in vivo, when the ratio between the number of cells from the biological material after and before administration is greater than 1, and preferably equal or greater than 2. The number of cells, or cell count, can be measured by any method well-known in the art, such as by flow cytometry.

In the context of the present invention, by "biological material", it is meant herein an organic material that can have a biological activity and that is normally used by a living organism for generation or maintenance of life. In the context of the invention, said material comprises cells as indicated above, and, as such, is preferably selected from the group consisting of cells, tissues, organs, derivatives thereof and combinations thereof, or in other words is preferably made of cells, tissues, organs, derivatives thereof, or combinations thereof. Said cells, tissues and organs can be natural, synthetic or engineered in vitro. For example, cells, tissues and organs can be engineered so as to express a transgene of interest. The biological material according to the invention is more particularly intended to be used for cell, tissue or organ regeneration in a subject in need thereof, and as such, can be of homologous (same species), heterologous (different species), autologous (same subject), or syngeneic origin (different subject of the same species, which is immunologically compatible, such as a twin). Autologous and syngeneic biological materials are herein particularly preferred in order to avoid immune rejection of the biological material.

Cells according to the invention can be selected among stem cells, differentiated cells, and combinations thereof, that can be administered, for example by way of cell therapy, to a subject in need thereof.

Examples of suitable stem cells according to the invention include, without limitation, embryonic stem cells; totipotent stem cells; pluripotent stem cells including notably induced pluripotent stem cells; multipotent stem cells; adult stem cells; progenitors and stem cells of any origin such as neuronal stem cells, myogenic stem cells (i.e. satellite cells, which are Pax7+ and CD34+), hematopoietic stem cells (HSCs), mesenchymal stem cells (MSCs), bone-marrow-derived MSCs, epithelial stem cells such as skin or intestinal stem cells, and adipose tissue-derived stem cells.

Particularly preferred stem cells according to the invention are myogenic stem cells, hematopoietic stem cells, and mesenchymal stem cells (MSCs); more preferably, myogenic stem cells and hematopoietic stem cells.

Examples of suitable differentiated cells according to the invention include, without limitation, cells of any origin such as neurons, myogenic cells (i.e. myoblasts or myocytes), hematopoietic cells, epithelial cells, osteoblasts, osteocytes, chondrocytes, blood cells, keratinocytes, melanocytes, fibroblasts, Merkel cells, Langerhans cells, adipocytes, and endothelial cells.

Particularly preferred differentiated cells according to the invention are myogenic cells, and hematopoietic cells.

Tissues according to the invention can be selected among any tissue that can be grafted to a subject in need thereof. Examples of suitable tissues according to the invention include, without limitation, brain tissue, nerve(s), muscle such as cardiac muscle, skeletal muscle, smooth muscle, or striated muscle, vascular tissue, blood, epithelium such as ovarium epithelium, testicular tissue, bone marrow, bone, cartilage, dental pulp, adipose tissue, retina, cornea, liver, and skin such as epidermis or dermis of the skin.

Particularly preferred tissues according to the invention are muscle such as cardiac muscle, skeletal muscle, smooth muscle, or striated muscle, vascular tissue, blood, and bone marrow.

Cell or tissue derivatives may also be used such as bone or cartilage substitutes (e.g. demineralized bone matrix, ceramics such as hydroxyapatite, tricalcium phosphate, coral, bioactive glasses, combinations thereof, etc), skin substitutes (e.g. Biobrane®, Transcyte®, Integra®, Alloderm®, Apligraf®, Dermagraf® to name a few, which are commercialized, among other by Smith & Nephew, Integra, LifeCell, Apligraf, and Dermagraft), cardiovascular tissue substitutes (Zimmerman et al., 2003; Neal et al., 2012; Lundberg et al., 2013; Li et al., 2013; Fernandez et al., 2014), smooth muscle substitutes, or nerve substitutes (Konofaos et al., 2013).

Finally, organs according to the invention can be selected among any organ that can be transplanted in a subject in need thereof. Examples of suitable organs according to the invention include, without limitation, any part of the neuronal system such as spinal cord, heart, blood vessels, fat, lungs, kidney, liver, pancreas, intestine, face, teeth, hands, legs, penis, uterus, testis, bone, skin, ligaments or thymus.

Particularly preferred organs according to the invention are heart and blood vessels.

According to a preferred embodiment, the biological material according to the invention comprises at least stem cells.

It is within the skill of the person in the art to select the appropriate biological material for the intended use, depending upon the cells, tissues or organs that need to be regenerated in a subject.

For example, in order to regenerate a part of the nervous system, the biological material is preferably selected from the group consisting of neuronal stem cells, neurons, nerves, brain tissue, spinal cord, and combinations thereof, and more preferably is neuronal stem cells.

As another example, in order to regenerate muscle, the biological material is preferably selected from the group consisting of myogenic stem cells, myogenic cells, muscle tissue and combinations thereof, and more preferably is myogenic stem cells.

As a further example, in order to regenerate blood tissue or bone marrow, or treat any hematopoietic system malfunction or disease in a subject in need thereof, the biological material is preferably selected from the group consisting of hematopoietic stem cells, blood cells, bone marrow and blood vessels, and more preferably is hematopoietic stem cells.

It is nevertheless well-known to the skilled person in the art that some stem cells have the capacity to differentiate in a variety of cell types. For example, mesenchymal stem cells can naturally give rise to bone tissue cells (osteoblasts and osteocytes), cartilage cells (chondrocytes), fat cells (adipocytes) and stromal cells that support blood formation (Goumans et al., 2014; Li et al., 2009). Besides, some stem cells can be reprogrammed, such as by transgenesis, in order to transdifferentiate, i.e. in order to differentiate into cell types other than those expected from their predicted lineage. For example, brain stem cells have shown the capacity to differentiate into blood cells or blood-forming cells that differentiate into cardiac muscle cells. Accordingly, the biological material can preferably be mesenchymal stem cells, in order to regenerate bone, cartilage, adipose tissue, or blood, or transdifferentiating brain stem cells in order to regenerate blood or cardiac muscle.

According to a preferred embodiment, the above method further comprises a step of preserving the biological material of the invention. Said step can be performed prior to the contact with the 5-hydroxytryptamine 1B receptor (5-HT1 BR)-stimulating agent, and/or concomitantly to said contact.

Indeed, the ability to preserve a biological material is critical for clinical applications relying on it, and also permits its storage until the patient is ready for administration thereof.

Methods for preserving the functional integrity of an isolated biological material prior to its administration to a subject are well-known in the art. For example, patent application WO 2011/151452 A1, incorporated herein by reference, describes a method for obtaining and preserving stem cells, while patent application U.S. Ser. No. 13/552,255 and US 20080057486 A1, incorporated herein by reference, describe methods for the preservation of tissues and/or organs. WO 2009068798 A1, incorporated herein by reference, further describes methods for protecting and/or preserving cells, tissues or organs.

For example, a biological material can be maintained in anoxic, or almost anoxic, conditions as described in patent application WO 2011/151452 A1. Preferably, said isolated biological material can be maintained at an oxygen concentration equal or less than 0.1%, and more preferably in the absence of any oxygen. Said maintenance can be preferably performed at 1 to 6° C., preferably at 3 to 5° C. and still preferably at 4° C. and/or during a period of time comprised between 12 hours to 60 days. Said maintenance can be preferably performed by culturing said biological material in a suitable chemically defined growth medium commonly used in the art. Said growth medium can be modified Eagle's medium (MEM), Dulbecco's modified Eagle's medium (DMEM), RPMI 1640 media, CMRL-1066 Medium, Ames' medium, Hams's F0 and F12 media, Leibovitz's, or Williams media, to name a few. Said growth medium can be liquid, semi-solid or solid (such as agar), and/or complemented or not with serum, growth factors and/or antibiotics.

In another aspect, the present invention is directed to an isolated biological material with enhanced in vivo engraftment potential, obtainable according to the method described above, preferably according to the ex vivo and/or in vitro method described above.

It must however be noted that the biological material with enhanced in vivo engraftment potential can also be obtained from a subject to which a 5-HT1 BR-stimulating agent is or has been administered.

Accordingly, in another aspect, the present invention is directed to a method for enhancing the in vivo engraftment potential of a biological material, comprising the step:
 a) isolating a biological material from a subject to which at least one 5-HT1 BR-stimulating agent is or has been administered.

The term "subject" refers throughout the specification to a human being or an animal, preferably to a human being. Herein, it should be understood that the subject from which the biological material is isolated is a subject intended to donate a biological material, i.e. a donor, as further defined below.

Nevertheless, as indicated above, the biological material can be autologous. According to this particular embodiment, the donor of the biological material will also be the recipient of said material.

In a particular embodiment, the subject from which a biological material is isolated is deceased and/or is not suffering from, or is not treated for, a migraine, headache and/or a psychiatric disorder, such as depression, anxiety or bipolar disorder, to name a few.

Still preferably, the above method can comprise the steps:
 b) further contacting in vitro and/or ex vivo said isolated biological material with said 5-HT1 BR-stimulating agent; and
 c) optionally, recovering said biological material Preferred embodiments are as described above.

In another aspect, the present invention is thus directed to an isolated biological material with enhanced in vivo engraftment potential, obtainable according to the method described above.

Yet, in another aspect, the present invention is directed to a 5-hydroxytryptamine 1B receptor (5-HT1 BR)-stimulating agent for use in a subject donating a biological material. More precisely, the invention relates to the use of a 5-hydroxytryptamine 1B receptor (5-HT1 BR)-stimulating agent for treating a subject donating a biological material. In other words, the invention relates to a method comprising the administration of at least one 5-hydroxytryptamine 1B receptor (5-HT1 BR)-stimulating agent to a subject donating a biological material.

By "subject donating a biological material", it is meant herein a donor of a biological material (as opposed to a recipient, i.e. a subject receiving the biological material), or in other words a subject whose biological material will be or is isolated from his/her body.

Nevertheless, as indicated above, the biological material can be autologous. According to this particular embodiment, it should be understood that the donor of the biological material will also be the recipient of said material.

In a particular embodiment, said subject is deceased and/or is not suffering from, or is not treated for, a migraine, headache and/or a psychiatric disorder, such as depression, anxiety or bipolar disorder.

It shall be further understood that the administration of the 5-HT1 BR-stimulating agent to said subject can be performed prior and/or simultaneously to the isolation of the biological material that is intended to be administered to a subject in need thereof (i.e. the recipient) as further described below.

According to a preferred embodiment, an effective amount of 5-HT1 BR-stimulating agent is used in the above method. By "effective amount", it is meant herein that the agent of the invention is administered to the subject in a quantity sufficient to provide the effect for which it is indicated, i.e. enhancement of the in vivo engraftment potential of the biological material that will be administered to a subject in need thereof (i.e. the recipient).

For example, said 5-HT1 BR-stimulating agent can be administered to the subject at an effective amount comprised between about 5 mg/kg and about 30 mg/kg, preferably between about 10 mg/kg and about 25 mg/kg, more preferably between about 15 mg/kg and about 20 mg/kg and preferably at 18 mg/kg.

Yet, according to a preferred embodiment, the above method is performed for an effective period of time. By "effective period of time", it is meant herein that the 5-HT1 BR-stimulating agent is administered to the subject for a period of time sufficient to provide the effect for which it is indicated, i.e. enhancement of the in vivo engraftment potential of the biological material that will be administered to a subject in need thereof (i.e. the recipient).

For example, said 5-HT1 BR-stimulating agent can preferably be administered to the subject for a period of about 6 weeks (in particular for slow-acting 5-HT1 BR-stimulating agents such as fluoxetine) or for a period of about 12 days (in particular for fast-acting 5-HT1 BR-stimulating agents such as vortioxetine).

Once generated, the isolated biological material with enhanced in vivo engraftment potential according to the invention can be used, if necessary, in a medical device, which can be administered to a patient in need thereof.

Therefore, it is another aspect of the present invention to provide a medical device, comprising at least the isolated biological material with enhanced in vivo engraftment potential according to the invention, and optionally at least one pharmaceutically acceptable excipient.

As used herein, the term a "pharmaceutically acceptable excipient" means an inactive or inert, and therefore nontoxic, component, as it has no pharmacological action, which can be used to improve properties of a composition, such as shelf-life, retention time at the application site, consumer acceptance, etc. It includes, without limitation, surfactants (cationic, anionic, or neutral); surface stabilizers; other enhancers, such as preservatives, wetting or emulsifying agents; solvents; buffers; salt solutions; dispersion medium; isotonic and absorption delaying agents, and the like; that are physiologically compatible.

The device can be in any form suitable for the intended use, such as in the form of a bandage or patch (for example to heal wounds), or of an implant (for example to repair a missing or impaired bone, cartilage, or tooth), in/on which the biological material can be incorporated/deposited.

The medical device according to the invention can further comprise at least one active agent, such as a therapeutic agent, which can further promote the in vivo engraftment of the biological material; or stimulate cell, tissue or organ regeneration; or even favor immunosuppression upon administration of the biological material in a subject in need thereof. For example, corticoids, cyclosporine, prednisone, mycophenolate mofetyl, everolimus, sirolimus, tracrolimus and/or azathioprine may be used as therapeutic agents favoring immunosuppression.

As mentioned above, the isolated biological material with enhanced in vivo engraftment potential according to the invention, or the medical device comprising said biological material, can be used in medical applications, which can benefit from the pro-engraftment capacities of said material, in particular regenerative medical applications, such as cell therapies, tissue grafts or organ transplants.

Thus, in another aspect, the invention provides the isolated biological material with enhanced in vivo engraftment potential or the medical device as described above, for use as a medicament. Preferred embodiments as described above apply herein mutatis mutandis.

In this regard, the invention preferably relates to the isolated biological material with enhanced in vivo engraftment potential or the medical device as described above, for use in a subject in need of cell, tissue or organ regeneration (i.e. recipient). More precisely, the present invention relates to the use of the isolated biological material or medical device according to the invention for treating a subject in need of cell, tissue or organ regeneration. In other words, the invention relates to a method comprising administering the isolated biological material or medical device of the invention, to a subject in need of cell, tissue or organ regeneration.

Still, preferably, the invention relates to the isolated biological material with enhanced in vivo engraftment potential or the medical device as described above, for use in the treatment of cell, tissue or organ loss, damage, or impairment in a subject in need thereof (i.e. recipient). More precisely, the present invention relates to the use of the isolated biological material or medical device of the invention in the treatment of cell, tissue or organ loss, damage, or impairment in a subject in need thereof. In other words, the invention relates to a method comprising administering the isolated biological material or medical device of the invention, to a subject in need of a treatment of cell, tissue or organ loss, damage, or impairment.

By "cell, tissue or organ regeneration", it is meant herein the regeneration or repair of one or several cells, tissues, or organs constituting the living body of a subject, such as the ones exemplified above.

The term "cell, tissue or organ loss, damage or impairment" encompasses herein any natural, congenital or acquired loss, damage or impairment (i.e. dysfunction) of cells, tissues or organs constituting the living body of a subject, such as the ones exemplified above. Said loss, damage or impairment can result, for example, from a natural aging process, a pathological disorder, and/or a trauma or injury to any part of the living body.

Examples of cell, tissue or organ loss, damage or impairment according to the invention include, without limitation:
  loss, damage or impairment of bone and/or cartilage, for example osteonecrosis, osteoporosis, bone fracture, periodontitis, loss of tooth, arthritis;

loss, damage or impairment of skin, for example skin lesion including skin redness or soreness, irritated skin, blisters and open wounds, burns, abscess and skin ulcer;

loss, damage or impairment of any part of the neuronal system, for example neurodegenerative disorders including Alzheimer's disease, fronto-temporal lobar atrophy, dementia with Lewy Bodies, Pick disease, dementia linked to chromosome, Parkinson disease, Progressive supranuclear palsy, multiple systeme atrophy, cortico-basal degeneration, Huntington disease, distonias, cerebellar ataxia, hereditary spastic paraparesis; primary disease of the white matter such as leukodystrophies and white matter diseases with inflammation such as multiple sclerosis; stroke; spinal cord injury;

loss, damage or impairment of muscle, for example genetic myopathies such as Duchenne muscular dystrophy, Becker muscular dystrophy, congenital muscular dystrophy, Limb Girdle muscular dystrophy (e.g. Myoshi or distal myopathy, dysferlinopathy, caveolinopathy, sarcoglynopathy, myotilinopathy), facioscapulohumeral muscular dystrophy, oculopharyngeal muscular dystrophy, myotonic muscular dystrophy, non-dystrophic myotonia, distal muscular dystrophy, Emery-Dreifuss muscular dystrophy; inherited myopathies such as nemaline myopathy, myo-tubular or centro-nuclear myopathy, central-core myopathy, Desmin myopathy, metabolic myopathies (e.g. lipid myopathies, mitochondrial myopathies and glycogen storage disorders such as Mc Ardle disease, pompe disease, or Tarui disease); acquired myopathies such as drug-induced myopathy, toxins-induced myopathies, trauma-induced myopathy, surgery-induced myopathy, disease-induced myopathy (e.g. cancers, viral or bacterial infections, endocrine disorders), diet-induced myopathy, age-related myopathies such as sarcopenia, urethral or anal sphincters incompetence, myocardial infarcts);

loss, damage or impairment of any part of the hematopoietic system, for example leukemias and lymphomas such as acute myelogenous leukemia, acute lymphoblastic leukemia, chronic myelogenous leukemia, chronic lymphocytic leukemia, juvenile myelomonocytic leukemia, Hodgkin's lymphoma, or non-Hodgkin's lymphoma; multiple myeloma and other plasma cell disorders; severe aplastic anemia and other marrow failure states, such as severe aplastic anemia, fanconi anemia, paroxysmal nocturnal hemoglobinuria (PNH), pure red cell aplasia, amegakaryocytosis/congenital thrombocytopenia; severe combined immunodeficiency (all sub-types) and other inherited immune system disorders, such as Wiskott-Aldrich syndrome; hemoglobinopathies, including beta thalassemia major, and sickle cell disease; Hurler's syndrome and other inherited metabolic disorders, such as Adrenoleukodystrophy and Metachromatic leukodystrophy; myelodysplastic and myeloproliferative disorders, such as refractory anemia (all types), chronic myelomonocytic leukemia, and agnogenic myeloid metaplasia (myelofibrosis); familial erythrophagocytic lymphohistiocytosis and other histiocytic disorders. Loss, damage or impairment of any part of the hematopoietic system can also indirectly be induced by treatments required in the above diseases or other diseases (e.g. such as solid tumors) in the need of bone marrow transplantation, such as hemotoxic ingestion or irradiation accidents.

Preferably, the cell, tissue or organ loss, damage or impairment to be treated according to the invention are selected from loss, damage or impairment of muscle and from loss, damage or impairment of the hematopoietic system, as described above.

The term "treating, "treatment" or "treat" as used herein encompasses, among other, preventing, ameliorating, inhibiting, or curing a deficiency, dysfunction, disease, or other deleterious process, including those that interfere and/or result from a therapy.

In the context of the present invention, a treatment intended for cell, tissue or organ regeneration, or a treatment of cell, tissue or organ loss, damage or impairment is herein preferably a cell therapy, a tissue graft or an organ transplant, depending on the nature of the biological material to be administered.

Said treatment can be performed on a subject in need of receiving the isolated biological material, as described above. In a particular embodiment, said subject is not suffering from, or is not treated for, a migraine, headache and/or a psychiatric disorder, such as depression, anxiety or bipolar disorder.

According to a preferred embodiment, a therapeutically effective amount of the isolated biological material is used in the above method. By "therapeutically effective amount", it is meant herein that the isolated biological material is administered in a quantity sufficient to provide the effect for which it is indicated, i.e. cell, tissue or organ regeneration and/or treatment of cell, tissue or organ loss, damage or impairment, without causing overly negative effects in the subject to which said material is administered. It is within the skill of the person in the art to determine the desired therapeutic amount of biological material to deliver by routine methods in the art.

For example, should the biological material be made of cells, in particular stem cells, preferred therapeutically effective amount according to the invention are at least about $1.0 \times 10^4$ cells/kg, more preferably at least about $5.0 \times 10^4$ cells/kg, at least about $1.0 \times 10^5$ cells/kg, still preferably at least about $5.0 \times 10^5$ cells/kg, at least about $1.0 \times 10^6$ cells/kg, even more preferably at least about $5.0 \times 10^6$ cells/kg, at least about $1.0 \times 10^7$ cells/kg, even more preferably at least about $5.0 \times 10^7$ cells/kg, at least about $1.0 \times 10^8$ cells/kg, at least about $5.0 \times 10^8$ cells/kg, and most preferably at least about $1.0 \times 10^9$ cells/kg.

The therapeutic effective amount of biological material to be administered may nevertheless vary according to the age and weight of the patient being treated; the nature of the cell, tissue or organ regeneration/of the loss, damage or impairment to be treated; and/or the mode of administration and frequency of administration.

Methods for administering to individuals the isolated biological material or medical device according to the invention are well known to those skilled in the art. Such methods include, but are not limited to, inoculation or injection or implantation (e.g., intra-muscular, subcutaneous, intra-articular, etc.), or topical application (e.g., on skin areas such as wounds, burns, etc.). A local injection to the site of interest can herein be particularly preferred. For example, should one wish to regenerate muscle, satellite cells can be injected intra-muscularly, and/or HSCs and/or MSCs can be injected intraveinously. Alternatively, should one wish to regenerate blood tissue or bone marrow, HSCs and/or MSCs can be injected intraveinously.

The inventors further demonstrated that a pre-treatment of a subject with a 5-hydroxytryptamine 1B receptor (5-HT1 BR)-stimulating agent, prior to a cell graft intended to regenerate muscle or bone marrow in said subject, can also enhance the in vivo engraftment potential of the grafted cells.

Accordingly, in another aspect, the present invention relates to a 5-hydroxytryptamine 1B receptor (5-HT1 BR)-stimulating agent, for a pre-therapeutic use in a subject in need of cell, tissue or organ regeneration. More precisely, the invention relates to the use of a 5-hydroxytryptamine 1B receptor (5-HT1 BR)-stimulating agent for pre-treating a subject in need of cell, tissue or organ regeneration. In other words, the invention relates to a method comprising the administration of at least one 5-hydroxytryptamine 1B receptor (5-HT1 BR)-stimulating agent, to a subject prior to a treatment intended to regenerate cells, tissues or organs in said subject.

Still preferably, the present invention relates to a 5-hydroxytryptamine 1B receptor (5-HT1 BR)-stimulating agent as described above, for use prior to the treatment of a cell, tissue, organ loss, damage or impairment in a subject in need thereof. More precisely, the invention relates to the use of a 5-hydroxytryptamine 1B receptor (5-HT1 BR)-stimulating agent prior to the treatment of a cell, tissue, organ loss, damage or impairment in a subject in need thereof. In other words, the invention relates to a method comprising the administration of at least one 5-hydroxytryptamine 1B receptor (5-HT1 BR)-stimulating agent to a subject in need of a treatment of a cell, tissue, organ loss, damage or impairment, prior to said treatment.

This means that this method can be performed while the subject is waiting for a treatment intended to regenerate its cells, tissues or organs, or in other words for a treatment of a cell, tissue or organ loss, damage or impairment.

Said subject can be a recipient waiting for the administration of a biological material.

In a particular embodiment, said subject is not suffering from, or is not treated for, a migraine, headache and/or a psychiatric disorder, such as depression, anxiety or bipolar disorder.

According to a preferred embodiment, an effective amount of 5-HT1 BR-stimulating agent is used in the above method. By "effective amount", it is meant herein that the agent of the invention is administered to the subject in a quantity sufficient to provide the effect for which it is indicated, i.e. regeneration of cells, tissues or organs or in other words treatment of a cell, tissue or organ loss, damage or impairment that will be performed, later on, to said subject.

For example, said 5-HT1 BR-stimulating agent can be administered to the subject at an effective amount comprised between about 5 mg/kg and about 30 mg/kg, preferably between about 10 mg/kg and about 25 mg/kg, more preferably between about 15 mg/kg and about 20 mg/kg and preferably at 18 mg/kg.

Yet, according to a preferred embodiment, the above method is performed for an effective period of time. By "effective period of time", it is meant herein that the 5-HT1 BR-stimulating agent is administered to the subject for a period of time sufficient to provide the effect for which it is indicated, i.e. regeneration of cells, tissues or organs or in other words treatment of a cell, tissue or organ loss, damage or impairment that will be performed, later on, to said subject.

For example, the 5-HT1 BR-stimulating agent can be preferably administered for at least 7 weeks, more preferably for at least 30 days, even more preferably for at least 10 to 20 days prior to performing a treatment intended for cell, tissue or organ regeneration, or in other words prior to the treatment of a cell, tissue, organ loss, damage or impairment. Should the 5-HT1 BR-stimulating agent be a slow-acting 5-HT1 BR-stimulating agent such as fluoxetine, said agent can for example be preferably administered for about 6 weeks, in order to achieve the desired effect. By contrast, should the 5-HT1 BR-stimulating agent be a fast-acting 5-HT1 BR-stimulating agent such as vortioxetine, said agent can for example be preferably administered for about 12 days, in order to achieve the desired effect.

The skilled person in the art would nevertheless readily understand that, in order to maximize the beneficial effect, the administration of the 5-hydroxytryptamine 1B receptor (5-HT1 BR)-stimulating agent can be pursued during and/or after the treatment intended to regenerate cells, tissues or organs in said subject, or in other words during and/or after the treatment of a cell, tissue or organ loss, damage or impairment.

According to this preferred embodiment, the invention relates to a 5-hydroxytryptamine 1B receptor (5-HT1 BR)-stimulating agent, for a pre-therapeutic use in a subject in need of a treatment intended for cell, tissue or organ regeneration, and co- and/or post-therapeutic use in said subject undergoing said treatment. More precisely, the invention relates to the use of a 5-hydroxytryptamine 1B receptor (5-HT1 BR)-stimulating agent for pre-treating a subject in need of a treatment intended for cell, tissue or organ regeneration, and for co- and/or post-treating said subject undergoing said treatment. In other words, the invention relates to a method comprising the administration of at least one 5-hydroxytryptamine 1B receptor (5-HT1 BR)-stimulating agent, to a subject prior to a treatment intended for cell, tissue or organ regeneration in said subject, and simultaneously and/or after said treatment.

In other words, the invention relates to a 5-hydroxytryptamine 1B receptor (5-HT1 BR)-stimulating agent as described above, for use prior to the treatment of a cell, tissue, organ loss, damage or impairment in a subject in need thereof, and simultaneously and/or after said treatment. More precisely, the invention relates to the use of a 5-hydroxytryptamine 1B receptor (5-HT1 BR)-stimulating agent prior to the treatment of a cell, tissue, organ loss, damage or impairment in a subject in need thereof, and simultaneously and/or after said treatment. In other words, the invention relates to a method comprising the administration of at least one 5-hydroxytryptamine 1B receptor (5-HT1 BR)-stimulating agent to a subject in need of a treatment of a cell, tissue, organ loss, damage or impairment, prior to said treatment, and simultaneously and/or after said treatment.

For example, the 5-HT1 BR-stimulating agent can be preferably further administered for at least 6 weeks, still preferably for at least 15 days, more preferably for at least 10 days, after performing a treatment intended for cell, tissue or organ regeneration, or in other words after the treatment of a cell, tissue, organ loss, damage or impairment. For illustrative purpose, said 5-HT1 BR-stimulating agent can preferably be administered to the subject for a period of about 6 weeks (in particular for slow-acting 5-HT1 BR-stimulating agents such as fluoxetine) or for a period of about 12 days (in particular for fast-acting 5-HT1 BR-stimulating agents such as vortioxetine).

The 5-hydroxytryptamine 1B receptor (5-HT1 BR)-stimulating agent according to the invention can also be employed for such pre-therapeutic use in a pharmaceutical composition which may comprise additional active agent(s).

Accordingly, in another aspect, the invention further provides a pharmaceutical composition for a pre-therapeutic use in a subject in need of cell, tissue or organ regeneration, wherein said composition comprises at least one 5-hydroxytryptamine 1B receptor (5-HT1 BR)-stimulating agent and at least one pharmaceutically acceptable excipient. More precisely, the invention relates to the use of said pharmaceutical composition for pre-treating a subject in need of cell, tissue or organ regeneration. In other words, the invention relates to a method comprising the administration of at least said pharmaceutical composition, to a subject prior to a treatment intended to regenerate cells, tissues or organs in said subject.

Preferably, the present invention relates to said pharmaceutical composition, for use prior to the treatment of a cell, tissue, organ loss, damage or impairment in a subject in need thereof. More precisely, the invention relates to the use of said pharmaceutical composition prior to the treatment of a cell, tissue, organ loss, damage or impairment in a subject in need thereof. In other words, the invention relates to a method comprising the administration of at least said pharmaceutical composition to a subject in need of a treatment of a cell, tissue, organ loss, damage or impairment, prior to said treatment.

Pre-therapeutic uses combined with a co- and/or post-therapeutic use of this composition are also herein encompassed.

According to this preferred embodiment, the invention relates to said pharmaceutical composition, for a pre-therapeutic use in a subject in need of a treatment intended for cell, tissue or organ regeneration, and co- and/or post-therapeutic use in said subject undergoing said treatment. More precisely, the invention relates to the use of said pharmaceutical composition for pre-treating a subject in need of a treatment intended for cell, tissue or organ regeneration, and for co- and/or post-treating said subject undergoing said treatment. In other words, the invention relates to a method comprising the administration of at least said pharmaceutical composition, to a subject prior to a treatment intended for cell, tissue or organ regeneration in said subject, and simultaneously and/or after said treatment.

According to a preferred embodiment, said pharmaceutical composition further comprises at least one active agent. The pharmaceutically acceptable excipient and/or active agent of said composition can be as described above.

Said pharmaceutical composition may preferably be in a form suitable for the purposes of the invention. For example, said composition may be in a form suitable for parenteral, oral (i.e. enteral or per os) or topical administration, such as a liquid suspension, a solid dosage form (granules, pills, capsules or tablets), or a paste or gel. The term parenteral as used herein includes subcutaneous, intravenous, or intramuscular injection.

An oral administration is herein particularly preferred. Nevertheless, a local injection to the site of interest (i.e. site to regenerate) can be performed, as an alternative or in addition to an oral administration. For example, should one wish to regenerate muscle, the composition can be injected intra-muscularly. Alternatively, should one wish to regenerate blood tissue or bone marrow, the composition can be injected intraveinously.

Preferred embodiments regarding the subject to be treated, the effective amount of 5-hydroxytryptamine 1B receptor (5-HT1 BR)-stimulating agent, and effective period of time for performing the method, as described above, apply mutatis mutandis for said pharmaceutical composition.

The skilled person in the art would further understand that the 5-hydroxytryptamine 1B receptor (5-HT1 BR)-stimulating agent can be administered either concomitantly to and/or after a treatment intended to regenerate cells, tissues or organs, or, in other words, after a treatment of a cell, tissue, or organ loss, damage or impairment, such as cell therapy, tissue graft or organ transplant.

Accordingly, in another aspect, the present invention relates to a 5-hydroxytryptamine 1B receptor (5-HT1 BR)-stimulating agent as described above, for a co-therapeutic and/or post-therapeutic use in a subject undergoing a treatment intended for cell, tissue or organ regeneration. More precisely, the invention relates to the use of a 5-hydroxytryptamine 1B receptor (5-HT1 BR)-stimulating agent for co-treating and/or post-treating a subject undergoing cell, tissue or organ regeneration. In other words, the invention relates to a method comprising the administration of at least one 5-hydroxytryptamine 1B receptor (5-HT1 BR)-stimulating agent to a subject undergoing a treatment intended to regenerate cells, tissues or organs, simultaneously and/or after said treatment.

Still preferably, the present invention relates to a 5-hydroxytryptamine 1B receptor (5-HT1 BR)-stimulating agent as described above, for use simultaneously and/or after the treatment of a cell, tissue, organ loss, damage or impairment in a subject. More precisely, the invention relates to the use of a 5-hydroxytryptamine 1B receptor (5-HT1 BR)-stimulating agent simultaneously and/or after the treatment of a cell, tissue, organ loss, damage or impairment in a subject. In other words, the invention relates to a method comprising the administration of at least one 5-hydroxytryptamine 1B receptor (5-HT1 BR)-stimulating agent to a subject undergoing a treatment of a cell, tissue, organ loss, damage or impairment, simultaneously and/or after said treatment.

Said subject can be a recipient to which a biological material is, or has been, administered.

In a particular embodiment, said subject is not suffering from, or is not treated for, a migraine, headache and/or a psychiatric disorder, such as depression, anxiety or bipolar disorder.

According to a preferred embodiment, an effective amount of 5-HT1 BR-stimulating agent is used in the above method. By "effective amount", it is meant herein that the agent of the invention is administered to the subject in a quantity sufficient to provide the effect for which it is indicated, i.e. regeneration of cells, tissues or organs or in other words treatment of a cell, tissue or organ loss, damage or impairment that is or has been performed to said subject.

For example, said 5-HT1 BR-stimulating agent can be administered to the subject at an effective amount comprised between about 5 mg/kg and about 30 mg/kg, preferably between about 10 mg/kg and about 25 mg/kg, more preferably between about 15 mg/kg and about 20 mg/kg and preferably at 18 mg/kg.

Yet, according to a preferred embodiment, the above method is performed for an effective period of time. By "effective period of time", it is meant herein that the 5-HT1 BR-stimulating agent is administered to the subject for a period of time sufficient to provide the effect for which it is indicated, i.e. regeneration of cells, tissues or organs or in other words treatment of a cell, tissue or organ loss, damage or impairment that is or has been performed to said subject.

For example, the 5-HT1 BR-stimulating agent can be preferably administered for at least 6 weeks, still preferably for at least 15 days, more preferably for that least 10 days, after performing a treatment intended for cell, tissue or organ regeneration, or in other words after the treatment of a cell, tissue, organ loss, damage or impairment. For illustrative purpose, said 5-HT1 BR-stimulating agent can preferably be administered to the subject for a period of about 6 weeks (in particular for slow-acting 5-HT1 BR-stimulating agents such as fluoxetine) or for a period of about 12 days (in particular for fast-acting 5-HT1 BR-stimulating agents such as vortioxetine).

The 5-hydroxytryptamine 1B receptor (5-HT1 BR)-stimulating agent according to the invention can also be employed for such co- and/or post-therapeutic use in a pharmaceutical composition which may comprise additional active agent(s).

Accordingly, in another aspect, the invention further provides a pharmaceutical composition for a co-therapeutic and/or post-therapeutic use in a subject undergoing a treatment intended for cell, tissue or organ regeneration, wherein said composition comprises at least one 5-hydroxytryptamine 1B receptor (5-HT1 BR)-stimulating agent and at least one pharmaceutically acceptable excipient. More precisely, the invention relates to the use of said pharmaceutical composition for co-treating and/or post-treating a subject undergoing cell, tissue or organ regeneration. In other words, the invention relates to a method comprising the administration of at least said pharmaceutical composition to a subject undergoing a treatment intended to regenerate cells, tissues or organs, simultaneously and/or after said treatment.

Still preferably, the present invention relates to said pharmaceutical composition as described above, for use simultaneously and/or after the treatment of a cell, tissue, organ loss, damage or impairment in a subject. More precisely, the invention relates to the use of said pharmaceutical composition simultaneously and/or after the treatment of a cell, tissue, organ loss, damage or impairment in a subject. In other words, the invention relates to a method comprising the administration of at least said pharmaceutical composition to a subject undergoing a treatment of a cell, tissue, organ loss, damage or impairment, simultaneously and/or after said treatment.

According to a preferred embodiment, said pharmaceutical composition further comprises at least one active agent. The pharmaceutically acceptable excipient and/or active agents of said composition can be as described above.

Said pharmaceutical composition may preferably be in a form suitable for the purposes of the invention. For example, said composition may be in a form suitable for parenteral, oral (i.e. enteral or per os) or topical administration, such as a liquid suspension, a solid dosage form (granules, pills, capsules or tablets), or a paste or gel. The term parenteral as used herein includes subcutaneous, intravenous, or intramuscular injection.

An oral administration is herein particularly preferred. Nevertheless, a local injection to the site of interest (i.e. site to regenerate) can be performed, as an alternative or in addition to an oral administration. For example, should one wish to regenerate muscle, the composition can be injected intra-muscularly. Alternatively, should one wish to regenerate blood tissue or bone marrow, the composition can be injected intraveinously.

Preferred embodiments regarding the subject treated, the effective amount of 5-hydroxytryptamine 1B receptor (5-HT1 BR)-stimulating agent, and effective period of time for performing the method, as described above, apply mutatis mutandis for said pharmaceutical composition.

The present invention further provides therapeutic methods regenerating cells, tissues or organs in a subject, by relying on the use of a biological material and a 5-hydroxytryptamine 1B receptor (5-HT1 BR)-stimulating agent.

Accordingly, in another aspect, the present invention relates to an isolated biological material (or a medical device comprising said material) and a 5-hydroxytryptamine 1B receptor (5-HT1 BR)-stimulating agent, as a combined preparation for simultaneous, separate or sequential administration in a treatment intended to regenerate cells, tissues or organs in a subject in need thereof (i.e. recipient). In other words, the invention relates to an isolated biological material (or a medical device comprising said material) and a 5-hydroxytryptamine 1B receptor (5-HT1 BR)-stimulating agent, as a combined preparation for simultaneous, separate or sequential administration in a treatment of a cell, tissue, organ loss, damage or impairment in a subject in need thereof (i.e. recipient).

More precisely, the invention relates to a method for cell, tissue or organ regeneration in a subject in need thereof, or to a method for treating a cell, tissue, organ loss, damage or impairment in a subject in need thereof, comprising:
 a) administering to said subject at least one 5-hydroxytryptamine 1B receptor (5-HT1 BR)-stimulating agent; and
 b) further administering to said subject at least one isolated biological material, or a medical device as described above, simultaneously, separately or sequentially to (i.e. before or after) step a).

According to a preferred embodiment, step b) is performed sequentially to (i.e. before or after) step a).

Yet, according to a preferred embodiment, the above method further comprises a step c) which consists of repeating step a). In other words, step a) can be further performed after step b).

In a particular embodiment, said subject is not suffering from, or is not treated for, a migraine, headache and/or a psychiatric disorder, such as depression, anxiety or bipolar disorder.

Preferred isolated biological materials and/or medical devices to be used in the above methods are as described above. Accordingly, the above methods can be a cell therapy, a tissue graft or an organ transplant. Most preferably, the biological material to be used in said methods is the biological material with enhanced in vivo engraftment potential, or the medical device comprising said material, as described above.

5-hydroxytryptamine 1B Receptor (5-HT1 BR)-Stimulating Agents

The different aspects and embodiments of the present invention relies on the use of 5-hydroxytryptamine 1B receptor (5-HT1 BR)-stimulating agents.

In this regard, by "5-hydroxytryptamine receptor", "5-HT receptor", "5-HT R" or "serotonin receptor", it is meant herein a superfamily of single-polypeptide-seven-transmembrane receptors, found in the central and peripheral nervous systems of almost all animals, that act through the activation of G protein signaling pathways (i.e. GPCRs) and/or as ligand-gated ion channels (i.e. LGICs). 5-hydroxytryptamine receptors are activated by their natural ligand, serotonin, in order to modulate the release of many neurotransmitters, such as glutamate, GABA, dopamine, epinephrine/norepinephrine, and acetylcholine, as well as many hormones such oxytocin, prolactin, vasopressin, cortisol, corticotropin, and substance P, among others.

The 5-hydroxytryptamine receptors are further categorized into 7 groups according to their G-protein coupling, among which the 5-HT1 and 2 groups, which are of a particular interest in the context of the present invention.

The "5-HT1 receptor" group comprises the 5-HT1 A, B, D, E and F subtypes, which share in humans between 40 to 63% structural homology, and preferentially couples to Gαi/o proteins. Activation of the 5-HT1 receptor subtypes typically elicits an inhibitory neurotransmission through activation of potassium channels, which decreases intracellular cAMP production.

Among the 5-HT1 receptor group, the "5-HT1 B receptor" ("5-hydroxytryptamine 1B receptor", "5-hydroxytryptamine receptor 1B", "5-HT-1B", "5-HT-1 D-beta", "serotonin 1 D beta receptor", or "serotonin receptor 1B") has been identified and characterized in 1992 by Jin et al. In humans, it is encoded by the HTB1R gene (NCBI RefSeq accession and version numbers NM_000863.1 and GI: 4504532; corresponding encoded protein: NCBI RefSeq accession and version numbers NP_000854.1 and GI:4504533), which is localized on chromosome 6 in position 6q13. The sequence of this receptor is highly conserved in humans, chimpanzee, Rhesus monkey, dog, cow, mouse, rat, chicken, zebrafish, *C. elegans*, and frog; and so far 135 organisms are known to have orthologs with the human gene HTR1B.

By "5-hydroxytryptamine 1B receptor (5-HT1 BR)-stimulating agent", or "5-HT1 BR-stimulating agent", it is meant herein an active agent capable of stimulating, either directly or indirectly, the activity of the 5-hydroxytryptamine 1B receptor, or in other words, capable of mimicking or enhancing the effects that are usually exerted by the natural ligand of said receptor (i.e. serotonin). A direct stimulation requires the binding of the agent to said receptor, while an indirect stimulation does not involve the binding of said agent to said receptor (i.e. it acts on the receptor via another mechanism of action). The capacity of a candidate agent to activate said receptor can be assessed by methods well-known in the art, for example by overexpressing 5-HT1 BR in cells and measuring intracellular cAMP production before and after contact of the recombinant cells with said candidate agent. Other methods for measuring the activity of 5-HT1 BR have been described in the art, and include, among others, a reverse phase high performance liquid chromatography coupled to an electrochemical detector (HPLC-ED) using an amperometric detector. In the context of the present invention, said agent can be selective for the 5-hydroxytryptamine 1B receptor, or may act not only on the 5-hydroxytryptamine 1B receptor but also on other receptors such as other 5-HT receptors.

According to the different aspects and embodiments of the invention described herein, the agent used in the present invention can either act directly or indirectly on said 5-HT1 BR.

According to a preferred embodiment, the 5-HT1 BR-stimulating agent used in the present invention is selected from the group consisting of antidepressant agents and antimigraine drugs, pharmaceutically acceptable derivatives, analogs, isomers, metabolites, salts, solvates, clathrates, polymorphs, and co-crystals thereof, and combinations thereof.

By "derivative", it is meant herein a compound that is directly derived from a chemical compound of interest (i.e. 5-HT1 BR-stimulating agent) and is structurally similar though non-identical to said compound, and which retains the same biological activity and/or physico-chemical properties.

By "analog", or "functional analog", it is meant herein a compound that is not directly derived from a chemical compound of interest and is thus structurally different, but exhibits the same biological activity and/or physico-chemical properties, such as isosters.

"Derivatives" and "analogs" of the 5-HT1 BR-stimulating agents according to the invention encompass herein compounds that retain the 5-HT1 BR-stimulating activity as defined above, but that do not cross the blood-brain barrier, as further described below.

By "isomer", it is meant herein a compound having the same chemical formula as a compound of interest, but a different chemical structure. This term encompasses structural isomers and stereoisomers. Should the isomer of the invention be a stereoisomer, the individual stereoisomers (enantiomers and diastereoisomers) and mixtures thereof are included within the scope of the invention. Some of the compounds according to the invention may exist in tautomeric forms (a type of structural isomer), which are also included within the scope of the invention.

By "metabolite" as used herein, it is meant any compound that is an intermediate and/or a product of metabolism. A metabolite from a chemical compound is usually formed as part of the natural biochemical process of degrading and eliminating the compound of interest in a subject to which it is administered. Examples of metabolites of antidepressant agents according to the invention are provided further below.

The term "pharmaceutically acceptable salt" or "salt as used herein refers to a salt that is physiologically tolerated (i.e. non-toxic) when used in an appropriate manner in the context of the present invention, particularly when used on mammals. Pharmaceutically acceptable salts include those derived from pharmaceutically acceptable inorganic and organic acids and bases. Examples of suitable acids according to the invention include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric, benzenesulfonic, gluconic, glutamic, bis-methylenesalicylic, ethanedisulfonic, propionic, p-amino-benzoic, malic, mandelic, cinnamic, citraconic, aspartic, stearic, palmitic, itaconic and sulfamic acids, as well as theophylline acetic acids and 8-halotheophyllines such as the 8-bromotheophylline. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal, (e.g., magnesium), ammonium and N—(C1-C4 alkyl)$_4^+$ salts.

The term "solvate" according to the invention should be understood as meaning any form of the active agent in accordance with the invention (i.e. 5-HT1 BR-stimulating agent), in which said compound is linked through non-covalent interactions to another molecule (normally a polar solvent), including especially hydrates and alcoholates, such as methanolate. Methods of solvation are well-known in the art.

By "clathrate", it is meant herein a chemical substance consisting of a lattice or cage that entraps or contains a second type of molecule/compound of interest, and which can be used to increase the stability and solubility in water of the molecule/compound of interest. Clathrates are typically polymeric.

The term "polymorphs" means herein different crystalline forms of a compound of interest in which molecules have different arrangements and/or different molecular conformation. It includes crystalline liquid form or crystalline solid form of a compound of interest. Hydrates and clathrates can be polymorphs.

By "co-crystal", it is meant herein a crystalline structure composed of at least two components, where the components may be atoms, ions or molecules. Solvates and clathrates may be co-crystals in certain conditions.

In the context of the present invention, the pharmaceutically acceptable derivatives, analogs, isomers, metabolites, salts, solvates, clathrates, polymorphs, and co-crystals as defined above are active, i.e. they exhibit a 5-HT1 BR-stimulating activity. Said activity can be assessed as described above.

It shall further be understood that the 5-HT1 BR-stimulating agents as described herein, or their derivatives, analogs, isomers, metabolites, salts, solvates, clathrates, polymorphs, and co-crystals are preferably in pharmaceutically acceptable or substantially pure form. By pharmaceutically acceptable form, it is meant, inter alia, having a pharmaceutically acceptable level of purity, i.e. excluding normal pharmaceutical additives, such as diluents and carriers, and any material considered toxic at normal dosage levels. In the context of the present invention, purity levels are preferably above 98%, more preferably above 99%, and even more preferably above 99.9%. In a preferred embodiment, said purity level is 99.9%.

As stated above, the 5-HT1 BR-stimulating agents according to the invention can be selected among antimigraine drugs, such as triptans or ergotamine. Triptans are well-known in the art as tryptamine-based drugs used in the treatment of migraines and cluster headaches, thanks to their agonistic effects on 5HT1 BR and 5HT1 DR. Examples of triptans according to the invention include, but are not limited to, sumatriptan, rizatriptan, zolmitriptan, eletriptan, almotriptan, frovatriptan, naratriptan avitriptan, and donitriptan. Non limitative examples of salts of said compounds are donitriptan hydrochloride, eletriptan hydrobromide, and rizatriptan benzoate.

Ergotamine:

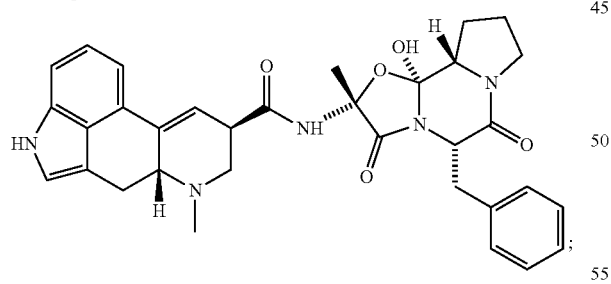

Sumatriptan:

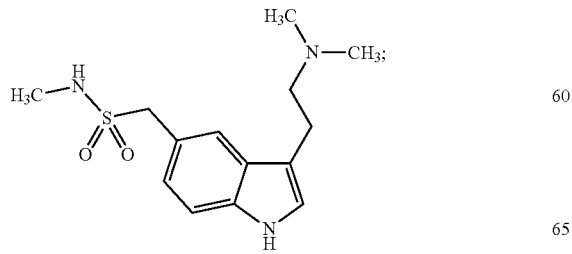

Rizatriptan:

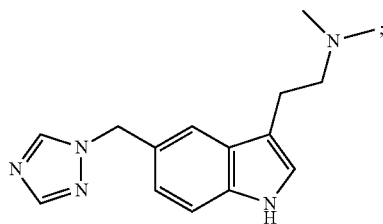

Zolmitriptan:

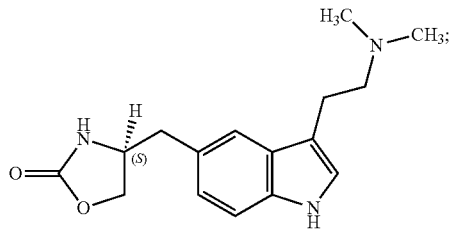

Eletriptan:

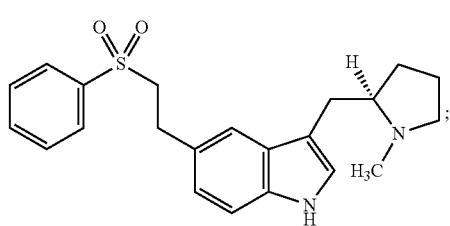

Almotriptan:

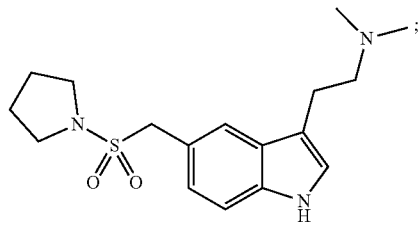

Frovatriptan:

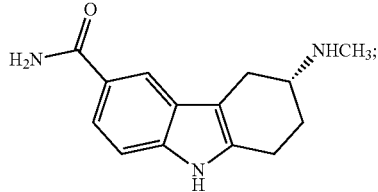

Naratriptan:

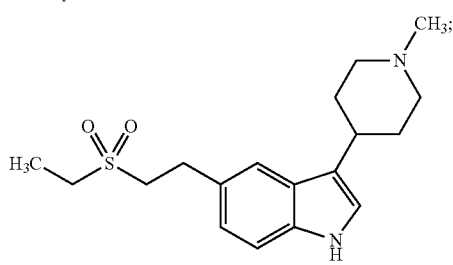

Avitriptan:

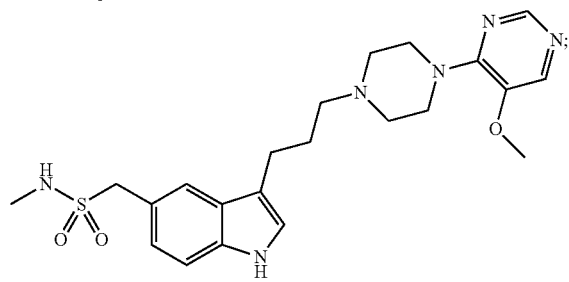

Donitriptan:

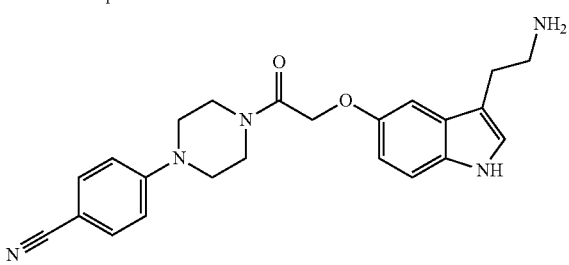

Particularly preferred triptans according to the invention are selected from the group consisting of sumatriptan, rizatriptan, zolmitriptan, eletriptan, almotriptan, and frovatriptan.

The 5-HT1 BR-stimulating agents according to the invention can alternatively be selected among antidepressant agents.

By "antidepressant agent", it is meant herein an active agent that is capable to treat mood disorders, such as depression (including severe depression) and/or dysthymia. Antidepressant agents according to the invention include, without limitation, serotonin reuptake inhibitors (SRIs); tricyclic antidepressants (TCAs); monoamine oxidase inhibitors (MAOs); noradrenergic and specific serotoninergic antidepressants (NaSSAs); atypical antidepressants or antidepressant enhancers.

Serotonin reuptake inhibitors (SRIs) designate a class of compounds that typically act by inhibiting the reuptake of the serotonin neurotransmitter into the presynaptic terminal, thereby increasing the serotonin extracellular level and thus serotoninergic transmission. Such compounds can act selectively or non-selectively on the neurotransmitter serotonin. SRIs can indeed also display various degrees of selectivity towards the other monoamine reuptake systems, in particular the transporters for norepinephrine and dopamine. SRIs typically include selective serotonin reuptake inhibitors (SSRIs), serotonine and norepinephrine reuptake inhibitors (SNRIs) and serotonin-norepinephrine-dopamine reuptake inhibitor (SNDRIs).

Examples of selective serotonin reuptake inhibitors (SSRIs) include, without limitation, fluoxetine, citalopram, escitalopram, sertraline, norsertraline, paroxetine, fluvoxamine, femoxetine, indalpine, alaproclate, cericlamine, ifoxetine, zimelidine, dapoxetine, and etoperidone, preferably fluoxetine, citalopram, escitalopram, sertraline, norsertraline, paroxetine, fluvoxamine, femoxetine, indalpine, alaproclate, cericlamine, ifoxetine, zimelidine, and dapoxetine.

Fluoxetine:

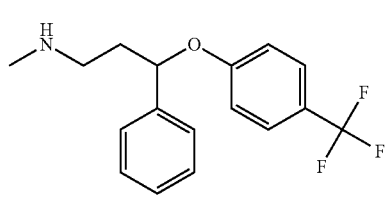

Citalopram:

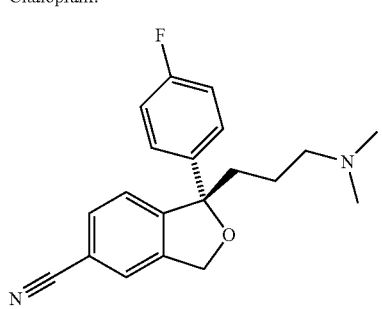

Examples of active SSRIs metabolites include, without limitation, desmethylcitalopram, didesmethylcitalopram, and seproxetine (i.e. (S)-norfluoxetine).

Examples of serotonine and norepinephrine reuptake inhibitors (SNRIs) include, without limitation, duloxetine, venlafaxine, desvenlafaxine, milnacipran, levominalcipran, and sibutramine.

Examples of serotonin-norepinephrine-dopamine reuptake inhibitor (SNDRIs) (also known as triple reuptake inhibitor or TRI) include, without limitation, bicifadine, brasofensine, tesofensine and nomifensine, preferably bicifadine.

Examples of tricyclic antidepressants (TCAs) according to the invention include, without limitation, clomipramine, amoxapine, nortriptyline, maprotiline, trimipramine, imipramine, desipramine and protriptyline.

Examples of monoamine oxidase inhibitors (MAOs) according to the invention include, without limitation, iproniazide, phenelzine, tranylcipromine, moclobemide, selegiline and rasagiline.

Examples of noradrenergic and specific serotoninergic antidepressants (NaSSAs), acting preferably by blocking presynaptic alpha-2 adrenergic receptors, include, among others, mirtazapine, mianserin, aptazapine, esmirtazapine, setiptiline and S32212 (also known as N-[4-methoxy-3-(4-methylpiperazin-1-yl)phenyl]-1,2-dihydro-3H-benzo[e]indole-3-carboxamide).

Examples of atypical antidepressants (defined as such as they do not belong to any of the foregoing classes of antidepressants) or antidepressant enhancers include, without limitation, bisarylsulfanyl amines such as vortioxetine, as well as tianeptine, agomelatine, nefazodone, trazodone, buspirone, tandospirone, and ketamine, preferably vortioxetine, tianeptine, agomelatine, nefazodone, trazodone, buspirone, tandospirone, and ketamine.

Bisarylsulfanyl amines have been disclosed in patent application WO 2003/029232, incorporated by reference, and are within the scope of the 5-HT1 BR-stimulating agents according to the invention. Said compounds can be described according to the following general formula (A):

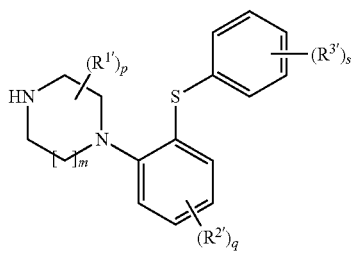

(A)

wherein
m is 1 or 2;
p is 0, 1, 2, 3, 4, 5, 6, 7 or 8;
q is 0, 1, 2, 3 or 4;
s is 1 or 2;
each $R^{1'}$ is independently selected from the group represented by $C_{1-6}$-alkyl, or two $R^{1'}$ attached to the same carbon atom may form a 3-6-membered spiro-attached cycloalkyl;
each $R^{2'}$ is independently selected from the groups represented by halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl, $C_{1-6}$-alk(en/yn)ylsulfonyl, or —NRxRy; —NRxCO—$C_{1-6}$-alk(en/yn)yl;
each $R^{3'}$ is independently selected from a group represented by halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, $C_{1-6}$-alk(en/yn)ylsulfonyl, aryl, $C_{1-6}$-alk(en/yn)yloxycarbonyl, acyl, —NR$^x$CO—$C_{1-6}$-alk(en/yn)yl, CONR$^x$R$^y$ or NR$^x$R$^y$;
or two adjacent $R^{3'}$ substituents together form a heterocycle fused to the phenyl ring selected from the group consisting of

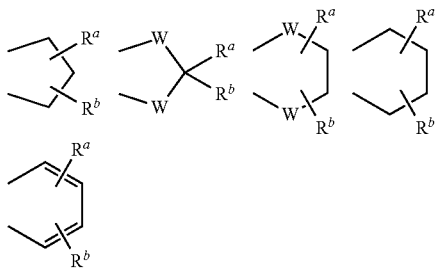

wherein W is O or S, and $R^a$ and $R^b$ are hydrogen or $C_{1-6}$-alkyl; or two adjacent $R^{3'}$ substituents together form a fused heteroaromatic system containing one, two or three heteroatoms,
wherein each $R^x$ and $R^y$ is independently selected from the group represented by hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, or aryl; or $R^x$ and $R^y$ together with the nitrogen to which they are attached form a 3-7-membered ring which optionally contains one further heteroatom;
or a pharmaceutically acceptable salt thereof.
Synthesis of compounds of general formula (A) is fully described in WO 2003/029232 and therefore does not need to be detailed herein.

A preferred embodiment of general formula (A) is wherein p is 0.
A preferred embodiment of general formula (A) is wherein m is 1 or 2.
A preferred embodiment of general formula (A) is wherein $R^{2'}$ is trifluoromethyl, or $C_{1-6}$-alkyl.
A preferred embodiment of general formula (A) is wherein $R^{3'}$ is selected from the group consisting of halogen, $C_{1-6}$-alkoxy, $C_{1-6}$-sulfanyl, $C_{1-6}$-alkyl hydroxy and trifluoromethyl.
A more preferred embodiment of general formula (A) is wherein m=1, p=0, q=0, $R^{3'}$ is methyl and s=2.
Particularly preferred embodiment of general formula (A) is wherein the compound of formula (A) is any of the following:
1-[2-(2-Trifluoromethylphenylsulfanyl)phenyl]piperazine,
1-[2-(4-Bromophenylsulfanyl)phenyl]piperazine,
1-{2-[4-(Methylsulfanyl)phenylsulfanyl]phenyl}piperazine,
1-[2-(4-Hydroxyphenylsulfanyl]phenyl}piperazine,
1-[2-(2,4-Dimethylphenylsulfanyl)phenyl]piperazine, also known as vortioxetine Vortioxetine:

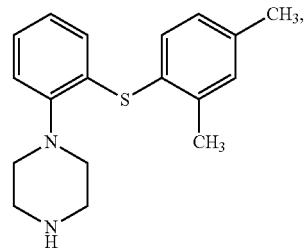

1-[2-(3,5-Dimethylphenylsulfanyl)phenyl]piperazine,
1-[2-(2,6-Dimethylphenylsulfanyl)phenyl]piperazine,
1-[2-(2,5-Dimethylphenylsulfanyl)phenyl]piperazine,
1-[2-(2-Trifluoromethylphenylsulfanyl)phenyl][1,4]diazepane,
1-[2-(3-Methylphenylsulfanyl)phenyl]-[1,4]-diazepane,
2-(4-Methylphenylsulfanyl)phenyl-1-piperazine,
1-[2-(4-Chlorophenylsulfanyl)phenyl]-piperazine,
1-[2-(4-Methoxyphenylsulfanyl)-4-chlorophenyl]piperazine,
1-[2-(4-Methoxyphenylsulfanyl)-4-methylphenyl]piperazine,
1-[2-(4-Methoxyphenylsulfanyl)-5-methylphenyl]piperazine,
1-[2-(4-Fluorophenylsulfanyl)-5-methylphenyl]piperazine,
1-[2-(4-Methoxyphenylsulfanyl)-5-trifluoromethylphenyl]piperazine,
1-[2-(4-Chlorophenylsulfanyl)phenyl]-3-methylpiperazine,
1-[2-(4-Chlorophenylsulfanyl)phenyl]-3,5-dimethylpiperazine,
or a pharmaceutically acceptable salt thereof.
Most preferred embodiment is wherein the compound of formula (A) is 1-[2-(2,4-Dimethylphenylsulfanyl)phenyl]piperazine (i.e. vortioxetine).
"Halogen" means herein fluoro (F), chloro (Cl), bromo (Br) or iodo (I).
"Alkyl", "alkenyl", "alkynyl", and "aryl" are further defined below.
The expression $C_{1-6}$-alk(en/yn)yl means a $C_{1-6}$-alkyl, $C_{2-6}$-alkenyl or a $C_{2-6}$-alkynyl group.

The expression $C_{3-8}$-cycloalk(en)yl means a $C_{3-8}$-cycloalkyl- or cycloalkenyl group.

The term $C_{1-6}$ alkyl refers to a branched or unbranched alkyl group having from one to six carbon atoms including but not limited to methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms, including one double bond and one triple bond respectively, including but not limited to ethenyl, propenyl, butenyl, ethynyl, propynyl and butynyl.

The term $C_{3-8}$ cycloalkyl designates a monocyclic or bicyclic carbocycle having three to eight C-atoms, including but not limited to cyclopropyl, cyclopentyl, cyclohexyl, etc.

The term $C_{3-8}$ cycloalkenyl designates a monocyclic or bicyclic carbocycle having three to eight C-atoms and including one double bond.

In the term $C_{3-8}$-cycloalk(en)yl-$C_{1-6}$-alk(en/yn)yl, $C_{3-8}$-cycloalk(en)yl and $C_{1-6}$-alk(en/yn)yl are as defined above.

The terms $C_{1-6}$-alk(en/yn)yloxy, $C_{1-6}$ alk(en/yn)ylsulfanyl, hydroxy-$C_{1-6}$-alk(en/yn)yl, halo-$C_{1-6}$-alk(en/yn)yl, halo-$C_{1-6}$-alk(en/yn)yloxy, $C_{1-6}$-alk(en/yn)ylsulfonyl etc. designate such groups in which the $C_{1-6}$-alk(en/yn)yl are as defined above.

As used herein, the term $C_{1-6}$-alk(en/yn)yloxycarbonyl refers to groups of the formula $C_{1-6}$-alk(en/yn)yl —O—CO—, wherein $C_{1-6}$-alk(en/yn)yl are as defined above.

As used herein, the term acyl refers to formyl, $C_{1-6}$-alk(en/yn)ylcarbonyl, arylcarbonyl, aryl-$C_{1-6}$-alk(en/yn)ylcarbonyl, $C_{3-8}$-cycloalk(en)ylcarbonyl or a $C_{3-8}$-cycloalk(en)yl-$C_{1-6}$-alk(en/yn)yl-carbonyl group.

The term 3-7-membered ring optionally containing one further heteroatom as used herein refers to ring systems such as 1-morpholinyl, 1-piperidinyl, 1-azepinyl, 1-piperazinyl, 1-homopiperazinyl, 1-imidazolyl, 1-pyrrolyl or pyrazolyl, all of which may be further substituted with $C_{1-6}$-alkyl.

The heterocycles formed by two adjacent $R^{3'}$ substituents and fused to the parent ring may together form rings such as 5-membered monocyclic rings such as 3H-1,2,3-oxathiazole, 1,3,2-oxathiazole, 1,3,2-dioxazole, 3H-1,2,3-dithiazote, 1,3,2-dithiazole, 1,2,3-oxadiazole, 1,2,3-thiadiazole, 1H-1,2,3-triazole, isoxazole, oxazole, isothiazole, thiazole, 1H-imidazole, 1H-pyrazole, 1H-pyrrole, furan or thiophene and 6-membered monocyclic rings such as 1,2,3-oxathiazine, 1,2,4-oxathiazine, 1,2,5-oxathiazine, 1,4,2-oxathiazine, 1,4,3-oxathiazine, 1,2,3-dioxazine, 1,2,4-dioxazine, 4H-1,3,2-dioxazine, 1,4,2-dioxazine, 2H-1,5,2-dioxazine, 1,2,3-dithiazine, 1,2,4-dithiazine, 4H-1,3,2-dithiazine, 1,4,2-dithiazine, 2H-1,5,2-dithiazine, 2H-1,2,3-oxadiazine, 2H-1,2,4-oxadiazine, 2H-1,2,5-oxadiazine, 2H-1,2,b-oxadiazine, 2H-1,3,4-oxadiazine, 2H-1,2,3-thiadiazine, 2H-1,2,4-thiadiazine, 2H-1,2,5-thiadiazine, 2H-1,2,6-thiadiazine, 2H-1,3,4-thiadiazine, 1,2,3-triazine, 1,2,4-triazine, 2H-1,2-oxazine, 2H-1,3-oxazine, 2H-1,4-oxazine, 2H-1,2-thiazine, 2H-1,3-thiazine, 2H-1,4-thiazine, pyrazine, pyridazine, pyrimidine, 4H-1,3-oxathiin, 1,4-oxathiin, 4H-1,3-dioxin, 1,4-dioxin, 4H-1,3-dithiin, 1,4-dithiin, pyridine, 2H-pyran or 2H-thiin.

Further, the compounds of general formula (A) may exist in unsolvated as well as in solvated forms with pharmaceutically acceptable solvents such as water, ethanol and the like, Some of the compounds of general formula (A) contain chiral centers and such compounds exist in the form of isomers (i.e. enantiomers). Such isomers and any mixtures thereof including racemic mixtures are also within the scope of the invention.

Particularly preferred antidepressant agents according to the invention are selected from the group consisting of bisarylsulfanyl amines as described above such as vortioxetine, and fluoxetine, citalopram, escitalopram, sertraline, paroxetine, fluvoxamine, femoxetine, indalpine, alaproclate, zimelidine, duloxetine, venlafaxine, desvenlafaxine, milnacipran, levominalcipran, sibutramine. bicifadine, clomipramine, amoxapine, maprotiline, imipramine, desipramine, moclobemide, selegiline, mirtazapine, mianserin, tianeptine, agomelatine, trazodone, buspirone, tandospirone, and ketamine. More preferably, antidepressant agents according to the invention are selected from the group consisting of bisarylsulfanyl amines as described above such as vortioxetine, and fluoxetine.

Other suitable 5-HT1 BR-stimulating agents according to the invention can be: anpirtoline hydrochloride, CGS-12066A, CGS 12066B dimaleate, oxymetazoline, 5-carboxamidotryptamine, CP-93129 and salts thereof such as CP-93129 dihydrochloride, CP-94253 and salts thereof such as CP-94253 hydrochloride, CP-122,288, CP-135,807, RU-24969 and salts thereof such as RU-24969 hemisuccinate, ziprasidone, asenapine, 5-nonyloxytryptamine oxalate, pindolol and/or (S)-(–)-pindolol, preferably anpirtoline hydrochloride, CGS-12066A, CGS 12066B dimaleate, oxymetazoline, 5-carboxamidotryptamine, CP-93129, CP-93129 dihydrochloride, CP-94253, CP-122,288, CP-135,807, RU-24969, ziprasidone, and/or asenapine.

According to a preferred embodiment, the 5-HT1 BR-stimulating agent used in the present invention is an antidepressant selected from the group consisting of atypical antidepressants and SRIs, in particular SSRIs.

More preferably, the 5-HT1 BR-stimulating agent of the present invention is the atypical antidepressant vortioxetine or the SSRI fluoxetine. Most preferably, the 5-HT1 BR-stimulating agent of the present invention is vortioxetine.

Nevertheless, in the event that the 5-hydroxytryptamine 1B receptor (5-HT1 BR)-stimulating agent of the present invention exerts undesired CNS-related adverse effects, it is particularly advantageous to limit the effects of said agent onto the peripheral serotonin system. Antidepressant agents are notably well-known for exerting such side effects. Side effects can be prevented by chemically modifying the structure of said agent, and by notably grafting a charged chemical moiety to prevent crossing of the blood-brain barrier.

Accordingly, in a preferred embodiment, the 5-HT1 BR-stimulating agent used in the present invention is modified to comprise at least one charged chemical moiety, preferably positively charged. Notably, the positive charge can be retained at a wide range of pH, in particular at a physiological pH.

In other terms, such modified 5-HT1 BR-stimulating agents according to the invention are not capable of crossing the blood-brain barrier. Antidepressant agents and antimigraine drugs modified in this manner are thus, respectively, anti-depressant disabled and antimigraine disabled.

Such chemical modifications have been extensively described in patent application WO 2007/148341, incorporated herein by reference, and can be performed so as to retain the 5-HT1 BR-stimulating activity of the compounds, while preventing them from crossing the blood-brain barrier.

The term "charged chemical moiety", "charged moiety", "charged chemical group" or "charged group", as used herein, refers to an atom or a group of atoms which forms a part of an organic molecule, and which is characterized by a positive or negative electrostatic charge.

By "positively charged chemical moiety", "positively charged moiety", "positively charged chemical group" or "positively charged group", it is thus meant herein a charged chemical moiety as defined above, which is characterized by a positive electrostatic charge. Compounds which include one or more positively charged moieties are molecular ions often referred to as molecular cations. A positively charged group of atoms has at least one electron less than the number of protons in these atoms. Positively charged chemical moieties include, without limitation, ammonium and sulfonium groups.

A positively charged group which retains its charge at physiological pH is a group that is not capable of participating in proton-exchange interactions at a pH range which is typical to the physiological environment in the body where the 5-HT1-BR stimulating agent is active. Typically, the physiological pH is about 7.4; therefore a positively charged group which retains its charge at physiological pH refers to a positively charged chemical group that stays ionized in a pH range of about 5-8. It is noted that even in the GI, where the pH level is extremely low in terms of physiological pH, the positively charged chemical moiety according to the invention remains positively charged, and hence modified 5-HT1-BR stimulating agents according to the present invention, are not adversely affected by the GI pH levels.

Still, yet, according to a further preferred embodiment, said positively charged chemical moiety is a quaternary ammonium group or a tertiary sulfonium group.

By "quaternary ammonium", it is meant herein a nitrogen atom which forms a part of a molecule (an amine) that is attached to four non-hydrogen substituents and thus is positively charged. The term "amine" describes a —NR'R" group where each of R' and R" is independently hydrogen, alkyl, cycloalkyl, heteroalicyclic, aryl or heteroaryl.

By "tertiary sulfonium group", it is meant herein a sulfur atom which forms a part of a molecule (a sulfonium) that is attached to three non-hydrogen substituents and thus is positively charged. The term "sulfonium" refers to a —S+R'R", wherein R' and R" are each independently alkyl, cycloalkyl, heteroacicyclic, aryl or heteroaryl.

According to the invention, the term "alkyl group" refers to a linear or branched saturated aliphatic group. Preferably, the alkyl group has 1 to 20 carbon atoms, and more preferably 1-10 carbon atoms, and even more preferably between 1-6 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. Examples of alkyl groups include, without limitation, methyl, ethyl, propyl, butyl, tert-butyl and isopropyl groups. The alkyl group can be further substituted. When substituted, the substituent can be, for example, an alkyl, an alkenyl, an alkynyl, a cycloalkyl, an aryl, a heteroaryl, a halide, a hydroxy, an alkoxy and a hydroxyalkyl. The term "alkyl", as used herein, further encompasses saturated or unsaturated hydrocarbon, hence this term further encompasses alkenyl and alkynyl.

The term "cycloalkyl" refers to an aliphatic monocyclic or bicyclic ring having 3 to 8 carbon atoms, and includes, without limitation cyclopropyl, cyclopentyl, cyclohexyl, etc.

The term "alkenyl" describes an unsaturated alkyl, as defined herein, having at least two carbon atoms and at least one carbon-carbon double bond, and which can be substituted by one or more substituents, as described above. The term "alkynyl" is an unsaturated alkyl having at least two carbon atoms and at least one carbon-carbon triple bond, and which can be substituted by one or more substituents, as described above.

The term "aryl" describes an all-carbon monocyclic or fused-ring polycyclic (i.e., rings which share adjacent pairs of carbon atoms) groups having a completely conjugated pi-electron system.

By "aryl or heteroaryl group", it is meant herein a mono- or polycyclic aromatic group comprising preferably between 4 and 15 carbon atoms, preferably between 5 and 10 carbon atoms. Examples of aryl groups include, without limitation, phenyl, naphtyl, etc. The aryl group according to the invention may be further substituted by one or more substituents, as described above. Heteroaryl groups typically comprise at least one heteroatom, such as nitrogen, oxygen, and sulfur—a heteroatom being any atom that is not carbon or hydrogen. Examples of heteroaryl groups include, without limitation, pyrrole, furane, thiophene, imidazole, oxazole, thiazole, pyrazole, pyridine, pyrimidine, quinoline, isoquinoline and purine. The heteroaryl group may be further substituted by one or more substituents, as described above; representative examples are thiadiazole, pyridine, pyrrole, oxazole, indole, purine and the like.

In a more preferred embodiment, said quaternary ammonium group has the formula (I)

—(NR₁R₂R₃)⁺Z⁻ (I)

wherein

Z is an organic or inorganic anion, such as NO₃⁻, H₂PO₄²⁻, Br—, HSO₄⁻, CH₃SO₃⁻, or tartaric acid anion; and R₁, R₂ and R₃ are each independently selected from the group consisting of alkyl, aryl and cycloalkyl.

Preferably, R₁, R₂ and R₃ are each an alkyl having from 1 to 4 carbon atoms, and more preferably, R₁, R₂ and R₃ are each methyl, resulting in the positively charged group, or the quaternary ammonium group —(NMe₃)⁺.

In another preferred embodiment, said tertiary sulfonium group has the formula (II)

—(SR₄R₅)⁺Z⁻ (II)

wherein

Z is an organic or inorganic anion, such as NO₃⁻, H₂PO₄²⁻, Br—, HSO₄⁻, CH₃SO₃⁻, or tartaric acid anion;

and R₄ and R₅ are each independently selected from the group consisting of alkyl, aryl and cycloalkyl.

Preferably, R₄ and R₅ are each an alkyl having from 1 to 4 carbon atoms, and more preferably, R₄ and R₅ are each methyl, resulting in the positively charged group, or the sulfonium —(SMe₂)⁺.

The positively charged group can be formed on the 5-HT1 BR-stimulating agent from an existing group which forms a part of the 5-HT1 BR-stimulating agent, namely, by turning a partially charged or uncharged group into a positively charged group, or by turning an existing positively charged group which can participate in proton-exchange interaction into one that cannot participate in such interaction, making it into an irreversible positive charge, or a permanent positive charge, thereby modifying the 5-HT1 BR-stimulating agent.

Alternatively, the positively charged group can be added to the 5-HT1 BR-stimulating agent by substituting one or more carbon atom with a positively charged group, e.g., by replacing a hydrogen atom or any other substituent with a quaternary ammonium or a tertiary sulfonium group.

Examples of preferred 5-HT1 BR-stimulating agents from which the compounds described herein can be derived include, without limitation, bisarylsulfanyl amines as described above such as vortioxetine, as well as fluoxetine, citalopram, alaproclate, dapoxetine, fluvoxamine, paroxetine, sertraline, venlafaxine, zimelidine, etoperidone, densvalafaxine, duloxetine, minalcipran, nefazodone, venlafaxine, brasofensine, tesofensine and nomifensine, preferably vortioxetine, fluoxetine, citalopram, alaproclate, dapoxetine, fluvoxamine, paroxetine, sertraline, venlafaxine and zimelidine. Indeed, all these agents already comprise at least one amine group, which can be readily converted into a quaternary ammonium, i.e. a positively charged group as defined above. In particular, said agents can be modified to comprise at least one quaternary ammonium group of formula (I) as described above.

An example of derivative of citalopram that comprises such a quaternary ammonium group is n-methyl-citalopram (NMC), of which the synthesis is fully detailed in patent application WO2007/128341.

Bisarylsulfanyl amines of formula (A) are also herein particularly advantageous as they comprise not only an amine group, but also a sulfur group, which can be readily converted into a quaternary ammonium group and/or into a tertiary sulfonium group, respectively. Positively charged moieties can also be attached to the carbon atom(s) of the piperazine group of said compounds.

Particularly preferred derivatives of said bisarylsulfanyl amines are compounds of formula (B) as follows:

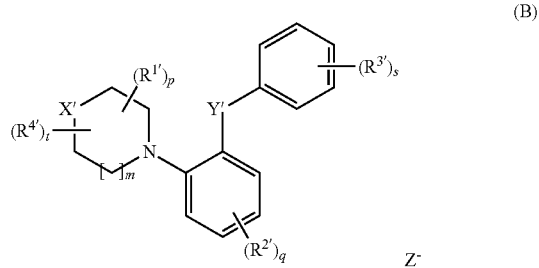

(B)

wherein

Z is an organic or inorganic anion as defined above, such as $NO_3^-$, $H_2PO_4^{2-}$, Br—, $HSO_4^-$, $CH_3SO_3^-$, or tartaric acid anion, or a mixture of organic or inorganic anions, whose global charge is such that the compound of formula (B) is neutral;

$R^{1'}$, $R^{2'}$, $R^{3'}$, m, p, q and s are as defined above, wherein $R^{3'}$ can optionally be a $C_{1-6}$-alk(en/yn)yloxy group substituted by an ammonium or sulfonium group as defined above, preferably $R^{3'}$ is choline;

t is 0, 1, 2, 3, 4, 5, 6, 7 or 8, preferably 0 or 1, more preferably 0, with the proviso that t+p≤8;

each $R^{4'}$ is at least one charged chemical moiety, identical or different, preferably positively charged, as defined above, such as a sulfonium or an ammonium group;

X' is selected from the group consisting of:
  —$(NR^{5'}R^{6'})^+$— wherein
    $R^{5'}$ and $R^{6'}$ are each independently selected from the group represented by hydrogen, alkyl, aryl and cycloalkyl as defined herein, preferably by an hydrogen, a $C_{1-6}$-alkyl, and a $C_{3-8}$-cycloalkyl; or
    $R^{5'}R^{6'}$ form together with the nitrogen to which they are attached a cycloheteroalkyl, preferably a 3-8-membered cycloheteroalkyl, more preferably a 3-6-membered cycloheteroalkyl;
  —NH—;
  —$NR^{7'}$— wherein $R^{7'}$ is a $C_{1-6}$-alkyl;
  —$N^+(O^-)R^{8'}$— wherein $R^{8'}$ is a $C_{1-6}$-alkyl;
  —$NC(O)R^{9'}$— wherein $R^{9'}$ is an amino acid, said amino-acid being preferably positively charged such as histidine, arginine or lysine, or an amino acid derivative, said derivative being preferably positively charged such as choline or carnitine, or a $C_{1-6}$-alkyl phosphonium;

Y' is selected from the group consisting of:
  —S—;
  —$(SR^{10'})^+$— wherein $R^{10'}$ is selected from the group represented by hydrogen, alkyl, aryl and cycloalkyl as defined herein, preferably is a $C_{1-6}$-alkyl; and
  $S^+(O)^-$—.

The skilled person in the art would readily understand that the anions Z are present to counterbalance the positive charges on the molecule. Accordingly, compounds of formula (B) comprise as many anions Z as necessary to neutralize the positive charges of the molecule. One skilled practitioner would further understand that when p>0 and t>0, $R^{1'}$ and $R^{4'}$ are attached to any of the carbon atoms of the heterocyclic ring, albeit to different carbons.

In a preferred embodiment, only one of X', Y', $R^{4'}$ (when t>0) and $R^{3'}$ (when substituted by an ammonium or sulfonium group) is a positively charged chemical moiety.

Preferred embodiments regarding $R^{1'}$, $R^{2'}$, $R^{3'}$, m, p, q and s are as defined above.

In a preferred embodiment of the invention, the 5-HT1 BR-stimulating agent from which the compounds described herein are derived, to notably preferably comprise a charged chemical moiety, is selected from the group consisting of atypical antidepressants such as bisarylsulfanyl amines as defined above and SRIs, in particular SSRIs.

More preferably, the 5-HT1 BR-stimulating agent to be modified is the atypical antidepressant vortioxetine or the SSRI fluoxetine. Most preferably, the 5-HT1 BR-stimulating agent to be modified is vortioxetine.

For example, vortioxetine can be chemically modified, as follows:

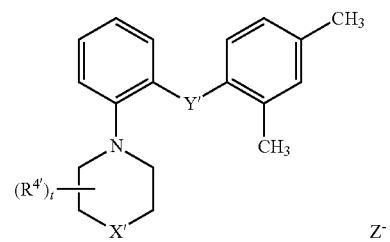

wherein Z, t, $R^{4'}$, X' and Y' are as defined above. More preferably, t=0.

Particularly preferred salts, derivatives and/or analogs of vortioxetine, which comprise at least one charged chemical moiety, preferably positively charged, are selected from the group consisting of:

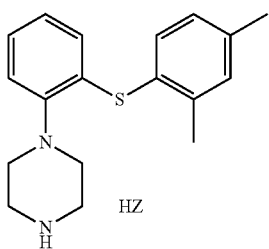
wherein HZ is preferably HNO₃, H₃PO₄, HBr, H₂SO₄, CH₃SO₃H, or tartaric acid (salts of vortioxetine);
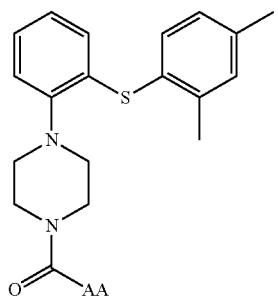
wherein AA is an amino acid, preferably
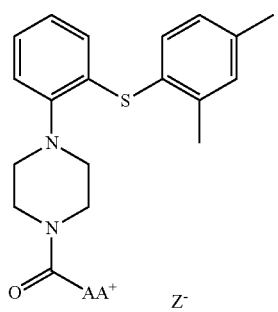
wherein AA+ is a positively charged amino acid such as histidine, arginine, or lysine;
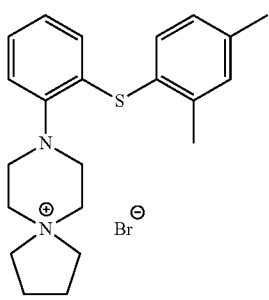 [SMILES: Cc1ccc(Sc2ccccc2N2CC[N+]3(CCCC3)CC2)c(C)c1 ; [Br-]]
(pyrrolidinium-vortioxetine);
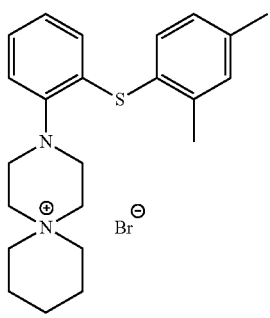 [SMILES: Cc1ccc(Sc2ccccc2N2CC[N+]3(CCCCC3)CC2)c(C)c1 ; [Br-]]
(pyperazinium-vortioxetine);
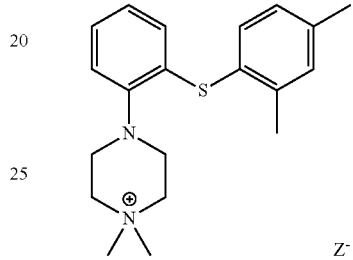
(dimethylammonium-vortioxetine);
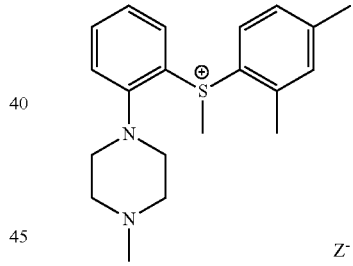
(sulfonium-vortioxetine);
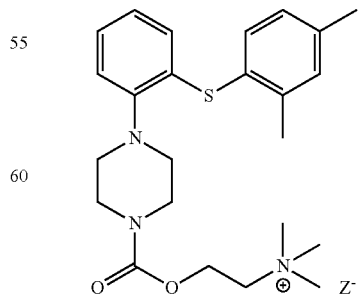
(choline-vortioxetine);

(benzyle-choline-vortioxetine);

(L-carnitine-vortioxetine);

(N-oxide-vortioxetine);

(sulfoxide-vortioxetine);

(phosphonium-vortioxetine); and (tempol-carbamate-vortioxetine).

Preferably, said salts, derivatives and/or analogs of vortioxetine, which comprise at least one charged chemical moiety, preferably positively charged, are selected from the group consisting of:
  salts of vortioxetine as described above;
  vortioxetine coupled to a positively charged amino acid (preferably at least one) such as histidine, arginine or lysine, as described above;
  pyrrolidinium-vortioxetine;
  pyperazinium-vortioxetine;
  dimethylammonium-vortioxetine;
  sulfonium-vortioxetine;
  N-oxide-vortioxetine;
  sulfoxide-vortioxetine;
  phosphonium-vortioxetine; and
  tempol-carbamate-vortioxetine.

More preferably, said salts, derivatives and/or analogs of vortioxetine, which comprise at least one positively charged chemical moiety, are selected from the group consisting of:
  salts of vortioxetine as described above;
  vortioxetine coupled to a positively charged amino acid (preferably at least one) such as histidine, arginine or lysine, as described above;
  pyrrolidinium-vortioxetine;
  pyperazinium-vortioxetine;
  dimethylammonium-vortioxetine;
  sulfonium-vortioxetine;
  N-oxide-vortioxetine;
  sulfoxide-vortioxetine; and
  phosphonium-vortioxetine.

Yet, even more preferably, said salts, derivatives and/or analogs of vortioxetine, which comprise at least one positively charged chemical moiety, are selected from the group consisting of:

salts of vortioxetine as described above;
vortioxetine coupled to a positively charged amino acid (preferably at least one) such as histidine, arginine or lysine, as described above;
pyrrolidinium-vortioxetine;
pyperazinium-vortioxetine;
dimethylammonium-vortioxetine;
sulfonium-vortioxetine; and
phosphonium-vortioxetine.

Still, even more preferably, said positively charged vortioxetine is selected from the group consisting of histidine-vortioxetine and pyrrolidinium-vortioxetine.

The above compounds can be prepared according to conventional methods in the art. Such methods are described in further details below.

For example, in order to synthetize pyrrolidinium-vortioxetine or pyperazinium-vortioxetine, one skilled person in the art can proceed as follows:

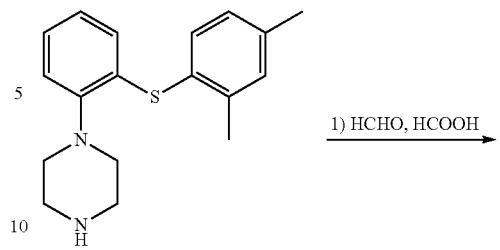

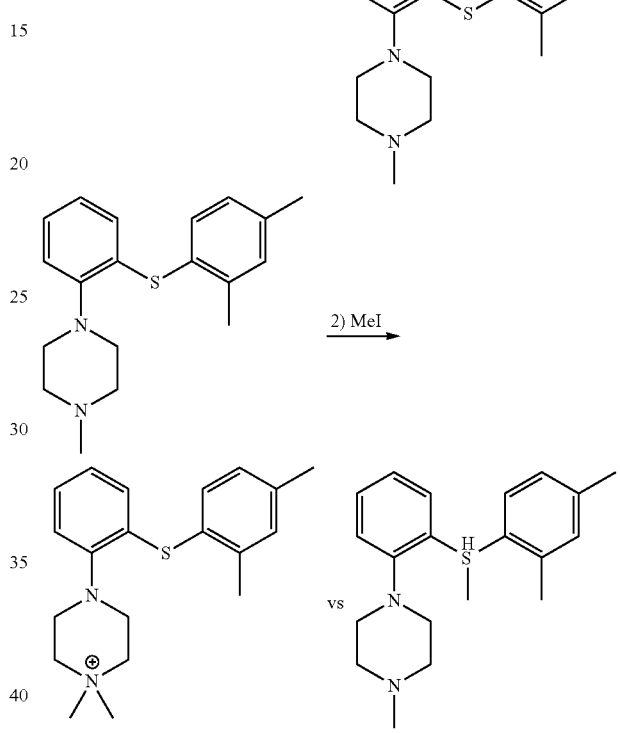

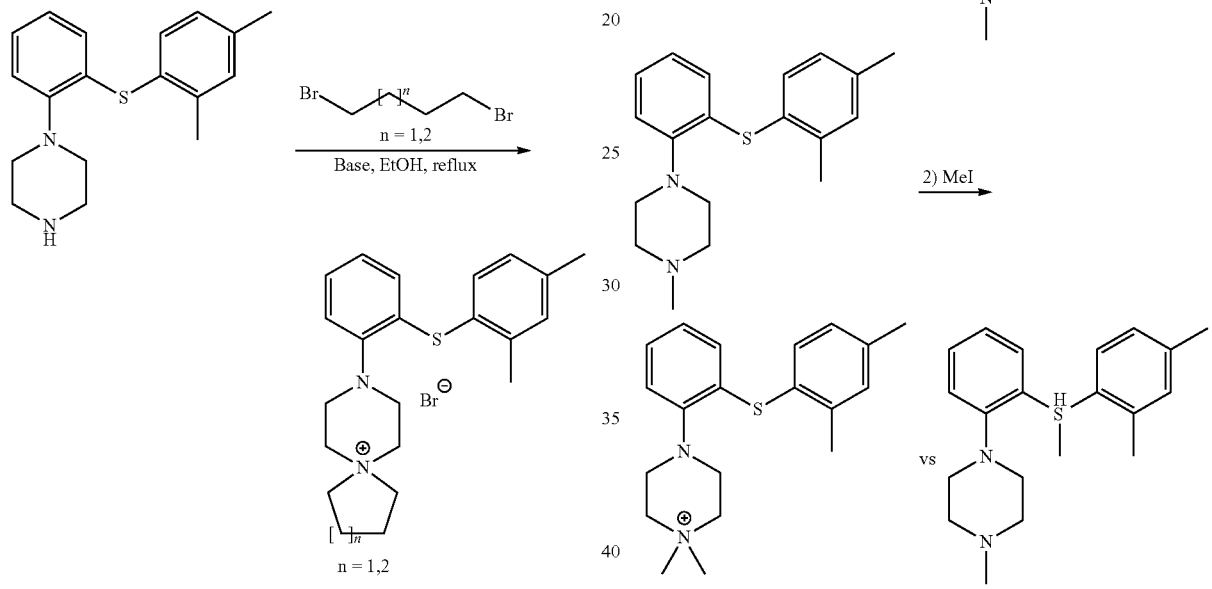

More particularly, for pyrrolidinium (n=1) formation on 4-arylpiperazine, the reaction can be performed using either K₂CO₃, ethanol (EtOH) and reflux for 10 h (Mokrosz et al., 1992, incorporated herein by reference), or K₂CO₃, acetone and reflux for 15 h (see WO 2004/9914A1, incorporated herein by reference).

Still, for example, in order to synthetize dimethylammonium-vortioxetine, one skilled person the art can proceed as follows:

More particularly, for 4-arylpiperazine dimethylation, one can refer to Romanelli et al. (2001, incorporated herein by reference), the first step being an Eschweiler-clarke reaction, and the second step being a methylation.

As another illustrative example, in order to synthetize amino acid derivatives of vortioxetine, choline-vortioxetine and carnitine-vortioxetine, one skilled person in the art can proceed as follows:

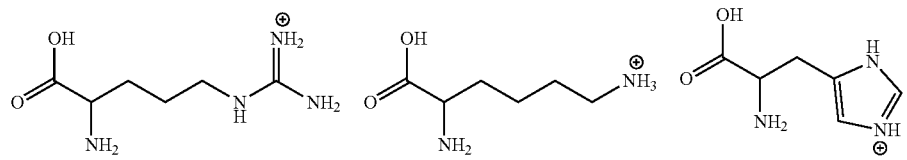

-continued

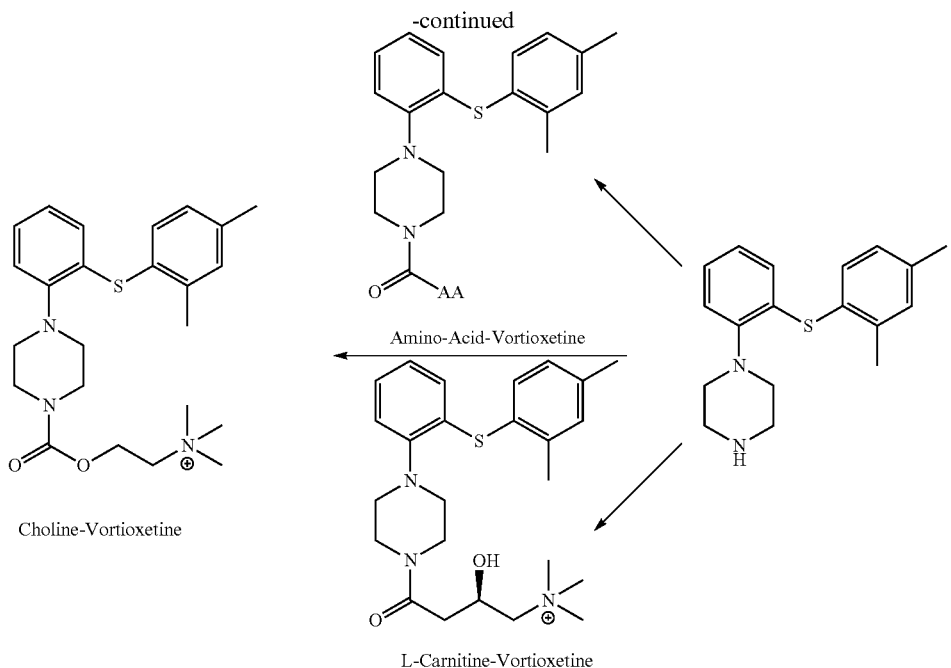

Choline-Vortioxetine

Amino-Acid-Vortioxetine

L-Carnitine-Vortioxetine

More particularly, for amide formation on the carnitine, the reaction can be performed on either acylhydrazine using pyridine, ethylene dichloride (EDC), dimethylformamide (DMF), and ethanol (EtOH) (Kuroda et al., 1996, incorporated herein by reference), or on primary amine using pyridine, ethylene dichloride (EDC), methanol (MeOH) and acetonitrile ($CH_3CN$) (Nakaya et al., 2001, incorporated herein by reference).

As another illustrative example, in order to synthetize phosphonium-vortioxetine, one skilled person in the art can proceed as follows:

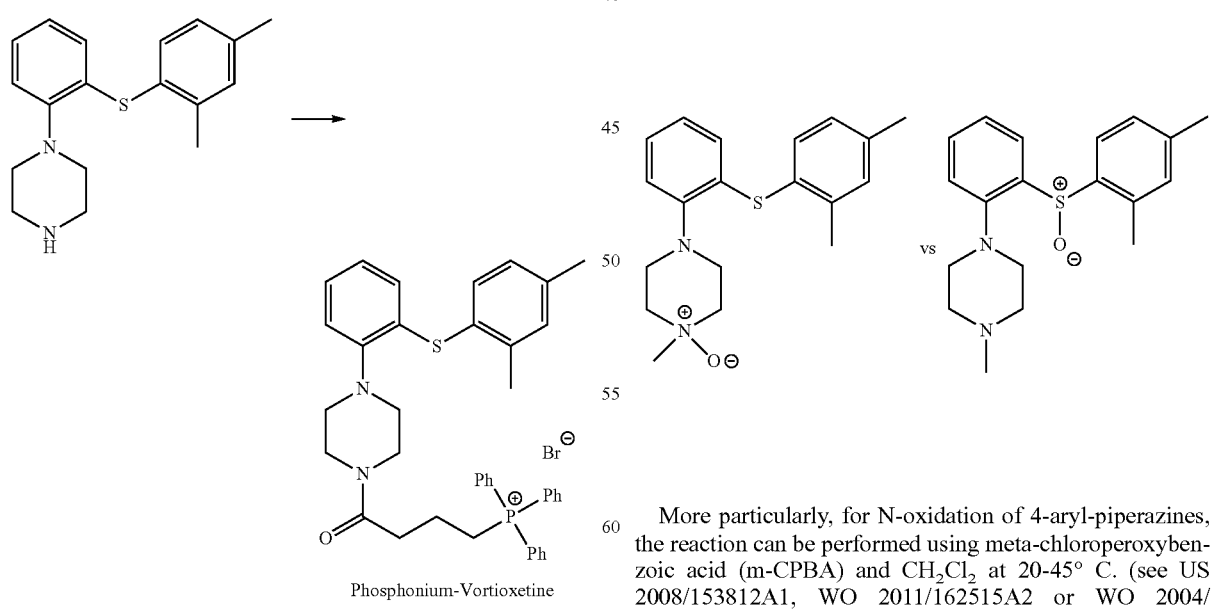

Phosphonium-Vortioxetine

As another illustrative example, in order to synthetize N-oxide-vortioxetine, one skilled person in the art can proceed as follows:

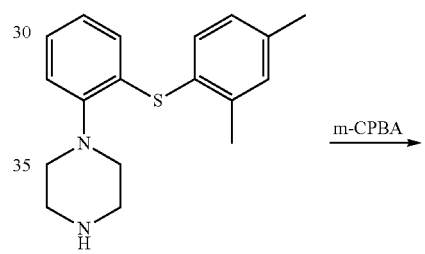

More particularly, for N-oxidation of 4-aryl-piperazines, the reaction can be performed using meta-chloroperoxybenzoic acid (m-CPBA) and $CH_2Cl_2$ at 20-45° C. (see US 2008/153812A1, WO 2011/162515A2 or WO 2004/104007A1, incorporated herein by reference).

As another illustrative example, in order to synthetize tempol-carbamate-vortioxetine, one skilled person in the art can proceed as follows:

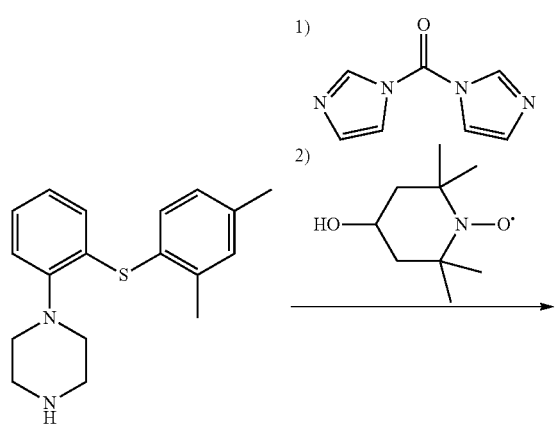
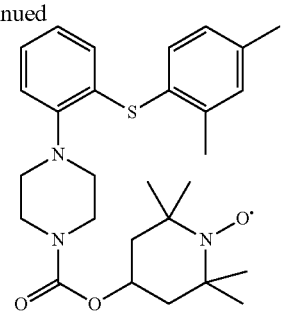
As another illustrative example, in order to synthetize benzyl-choline-vortioxetine, one skilled person in the art can proceed as follows:
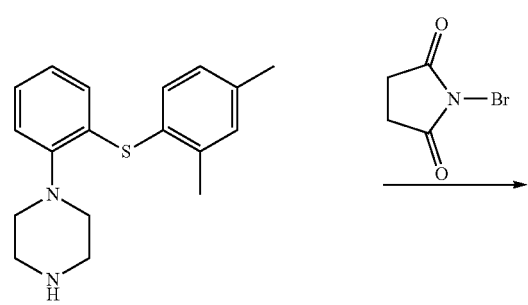
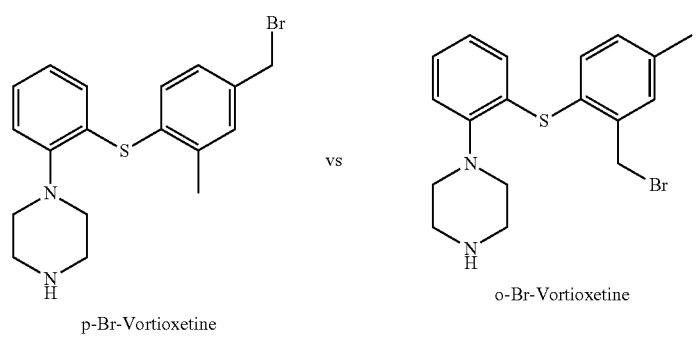
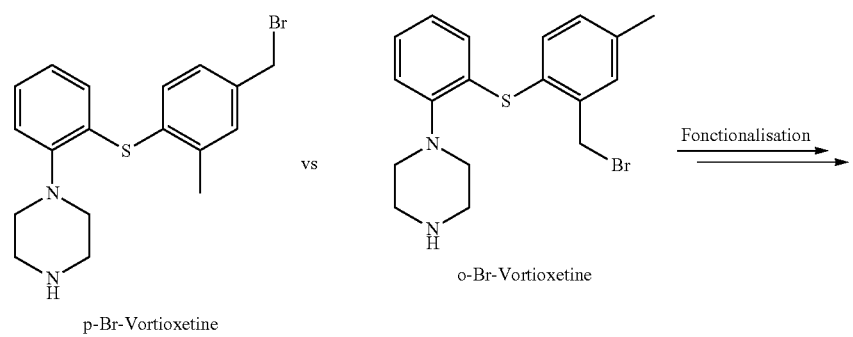

-continued

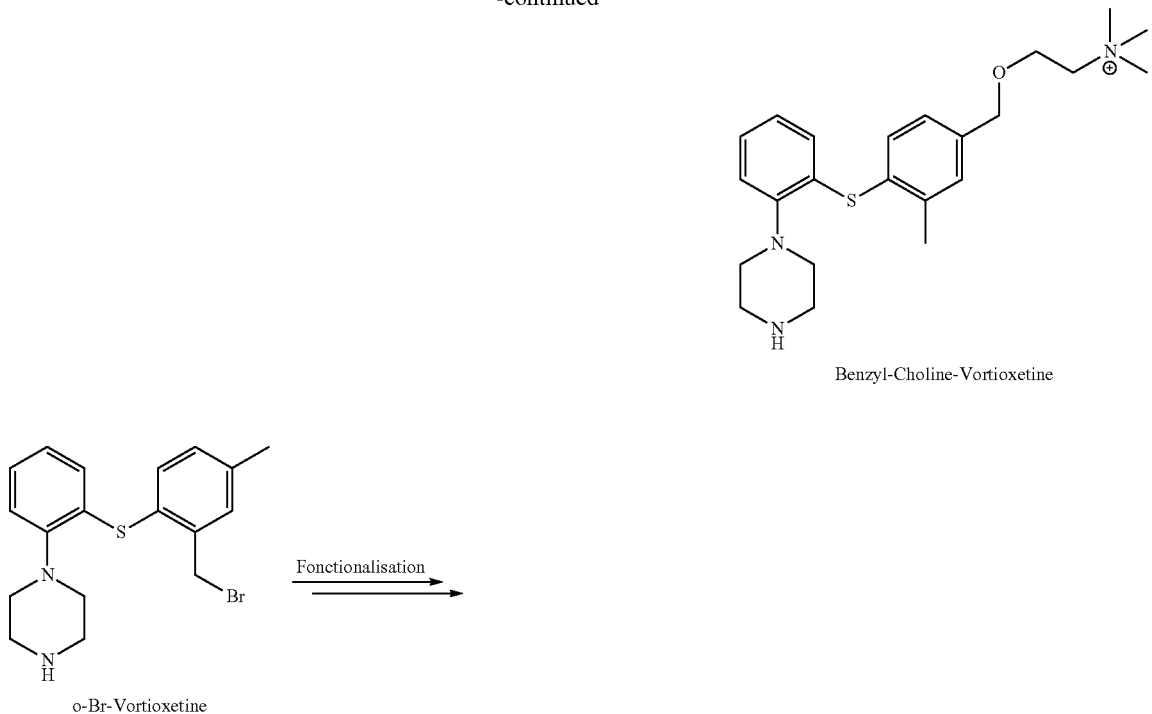

Benzyl-Choline-Vortioxetine o-Br-Vortioxetine

More particularly, for benzylic position bromation, the reaction can be performed using either N-bromosuccinimide, azobisisobutyronitrile (AIBN) and tetrachloromethane ($CCl_4$) (see US 2010/4159A1, incorporated herein by reference), or N-bromosuccinimide, meta-chloroperoxybenzoic acid (m-CPBA) and tetrachloromethane ($CCl_4$) (see Farmaco, 1989, 44, from p. 683, incorporated herein by reference).

The present invention will be better understood in the light of the following detailed description of experiments, including examples. Nevertheless, the skilled artisan will appreciate that this detailed description is not limitative and that various modifications, substitutions, omissions, and changes may be made without departing from the scope of the invention.

EXAMPLES

Figure 1:
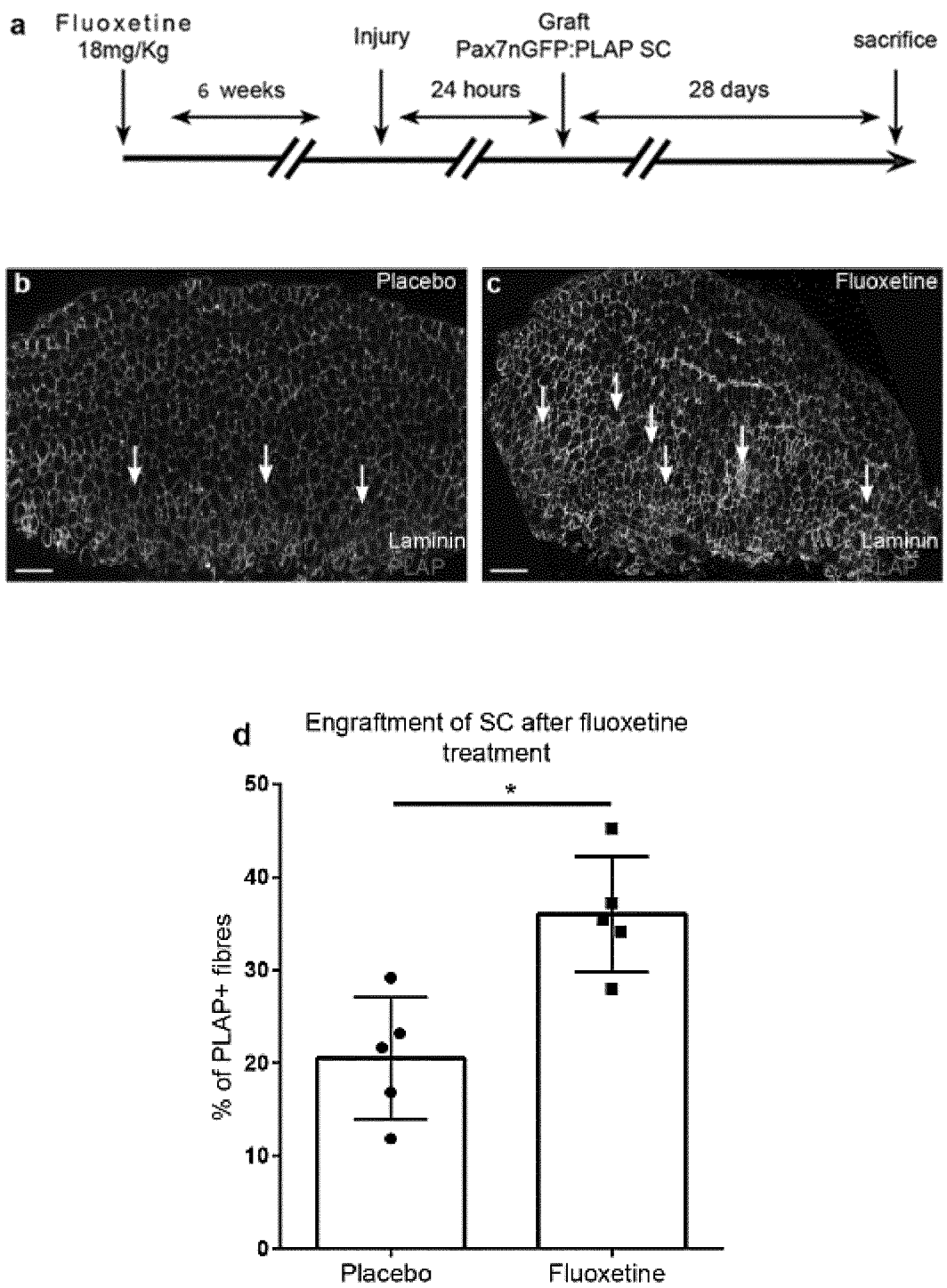
FIG. 1: Fluoxetine and vortioxetine increase the engraftment potential of the muscle stem cells. (a) Scheme of injection of fluoxetine. $Rag^{-/-}\gamma C^{-/-}$ mice were treated with fluoxetine for 6 weeks, injured with cardiotoxin and grafted 24 hours post-injury with FACS cell sorted satellite cells. 28 days post injury mice were sacrificed and tibialis anterior were fixed. (b-c) Transversal cut of the tibialis anterior immunostained with Laminin and PLAP on (b) placebo and (c) fluoxetine treated mice. (d) Histogram representing the percentage of PLAP+ fibres among all the fibres in placebo and fluoxetine treated animals. (e) Scheme of injection of vortioxetine. $Rag^{-/-}\gamma C^{-/-}$ mice were treated with vortioxetine for 12 days, injured with cardiotoxin and grafted 24 hours post-injury with FACS cell sorted satellite cells. 28 days post injury mice were sacrificed and tibialis anterior were fixed. (f-g) Transversal cut of the tibialis anterior immunostained with Laminin and PLAP on (f) placebo and (g) vortioxetine treated mice. (h) Histogram representing the percentage of PLAP+ fibres among all the fibres in placebo and fluoxetine treated animals. Means±SD are displayed * $p<0.05$.
Figure 1:
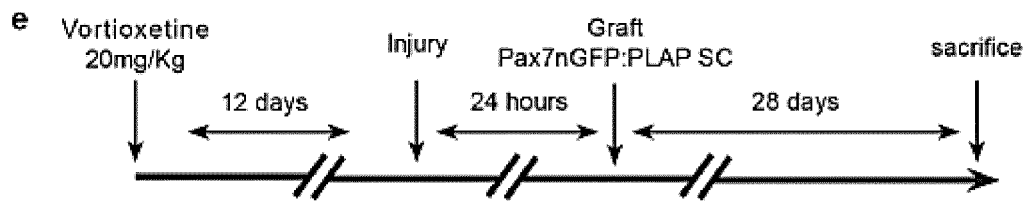
Figure 1:
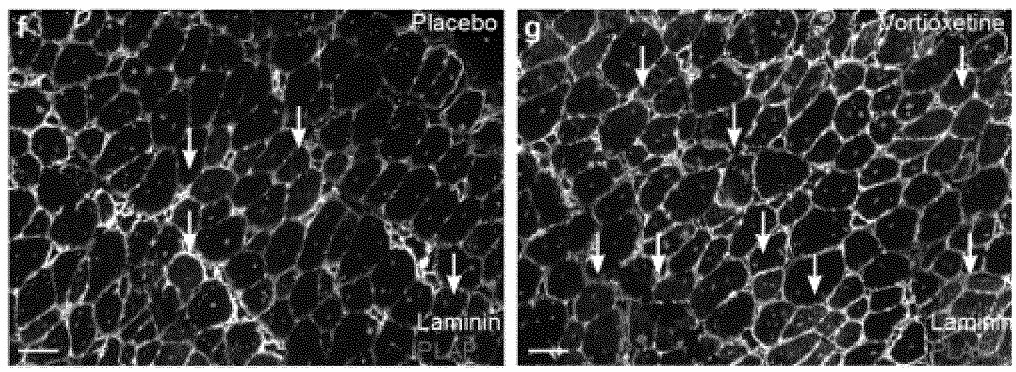
Figure 1:
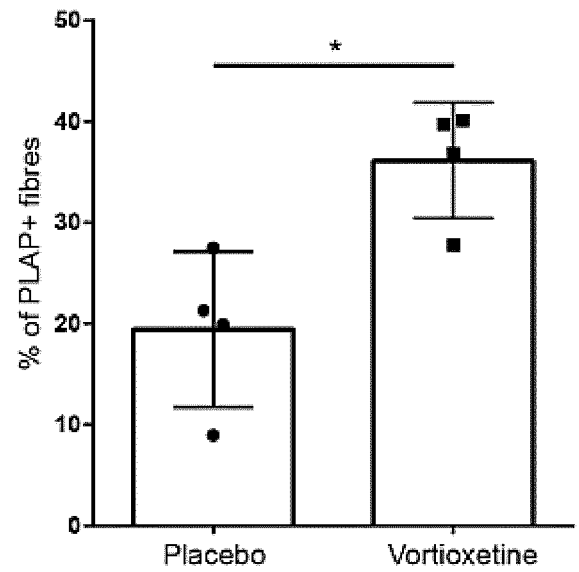

Fluoxetine and Vortioxetine Improve the Engraftment Potential of Muscle Stem Cells and Hematopoietic Stem Cells 1. Material and Methods
1.1. Mice Injection and Injury All protocol used were approved by local ethic comity. Mice were anesthetised and injured with cardiotoxin 18 hours before grafting in the tibialis anterior. Before grafting the mice were anesthetised again and grafted with 10,000 cells in 40 nl in PBS. Mice were kept for 28 days until muscle regeneration was complete. For bone marrow grafting, mice were irradiated at 95 cGy and grafted intra venous with non-irradiated bone marrow. Mice were sacrificed 5 weeks after the injection.

1.2. Histological Analysis

Tibialis anterior was carefully dissected and snap frozen in liquid-nitrogen-cooled isopentane for a few minutes and stored at $-80°$ C. prior to cryosectioning (10 μm sections). Sections were kept at room temperature overnight before staining. Sections were then rehydrated in PBS for 10 minutes and fixed in 10% formalin for 3 minutes. The sections were then routinely stained with PLAP antibody manually.

The slides were assessed by double blinding and automated when possible.

1.3. FACS Analysis

For bone marrow analysis, animals were sacrificed and bone marrow was flushed and filtered through 40 μm cell strainer. The bulk was then directly assessed using Gallios A94303 (Beckman Coulter) and analysed with Kaluza flow cytometry software.

1.4. Image Analysis

For image analysis, ImageJ 1.46r software was using between 10 different photos randomly taken per section and 3 sections minimum per experimental group. The pictures were converted in a binary image and then the pixel values were collected. For fibre size, the sections were immunostained with rabbit anti Laminin (Sigma-Aldrich #L9393) diluted at 1/200, overnight at 4° C. Secondary Donkey ant Rabbit 488 (DL488 JacksonImmuno #711486152) were used at 1/200 45 minutes at room temperature. The fibre perimeter was done automatically by using Pixcavator® software.

1.5. Statistical Analysis

Statistical analysis was performed using GraphPad Prism software using appropriate tests (non-parametric Mann-Whitney unless specified) and a minimum of 95% confidence interval for significance; p values indicated on figures are <0.05 (*), <0.01(), and <0.001 (*). Figures display average values of all animals tested ±SD or ±SEM for RT-qPCR, or as indicated.

2. Results
2.1. Fluoxetine and Vortioxetine Treatment Triggers an Increase in Engraftment Potential of Muscle Stem Cells in an Injured Paradigm In order to investigate the potential effect of fluoxetine and vortioxetine on the muscle engraftment potential, $Rag^{-/-}\gamma C^{-/-}$ immunodeficient mice (Sanchez et al., 2013) were used in this study. Mice were injured with cardiotoxin in the tibialis anterior (TA) and injected with 10,000 satellite cells (SC) 24 hours after the injury. The satellite cells (SC) were obtained from Tg:Pax7nGFP::PLAP mice (Deprimo et al., 1996; Rocheteau et al., 2012), allowing the prospective isolation of a pure population of SC by FACS (Pax7 being a specific marker of SC) and the follow up (PLAP placental alkaline phosphatase being an ubiquitous marker). The TA had been sampled 28 days post engraftment and the number of PLAP fibres was counted.

The $Rag^{-/-}\gamma C^{-/-}$ were treated for 6 weeks with fluoxetine per os at 18 mg/Kg at the time of the graft and the treatment continued during the regeneration process (FIG. 1a). When regeneration was completed 28 days post injury, the percentage of PLAP positive fibres was 20.5%±6.5 against 36%±6.2 in the treated animals (p=0.016; n=5, FIG. 1b-d). In other words, the engraftment potential of the injected SC almost doubled when injected in fluoxetine treated animals.

To investigate the potential effect of vortioxetine on the engraftment potential, the same approach was used. The $Rag^{-/-}\gamma C^{-/-}$ were treated for 12 days by intra peritoneal injections at 20 mg/Kg. Twelve days after the beginning of the treatment, the mice were injured and grafted with Pax7nGFP:PLAP SC. The treatment was continuous during the entire regenerative process (FIG. 1e). 28 days post injury the TA were sampled and stained for Laminin and PLAP. 19%±7.7 fibres were PLAP+ after placebo treatment against 36.1%±5.7 in the vortioxetine treated animals (p=0.028, n=4, FIG. 1f-h). In other words, the engraftment potential of the injected SC more than doubled when injected in vortioxetine treated animals.

2.2. Fluoxetine and Vortioxetine Treatment Triggers an Increase in Engraftment Potential of the Bone Marrow after Irradiation In order to investigate the potential effect of fluoxetine and vortioxetine on the bone marrow engraftment potential, $Rag^{-/-}\gamma c^{-/-}$ immunodeficient mice were used. These mice were irradiated at 95 cGy and then injected intravenously with 2 million cells taken from Tg:ActinGFP mouse (Okabe et al., 1997), to track the fate of the grafted cells.

Figure 2:
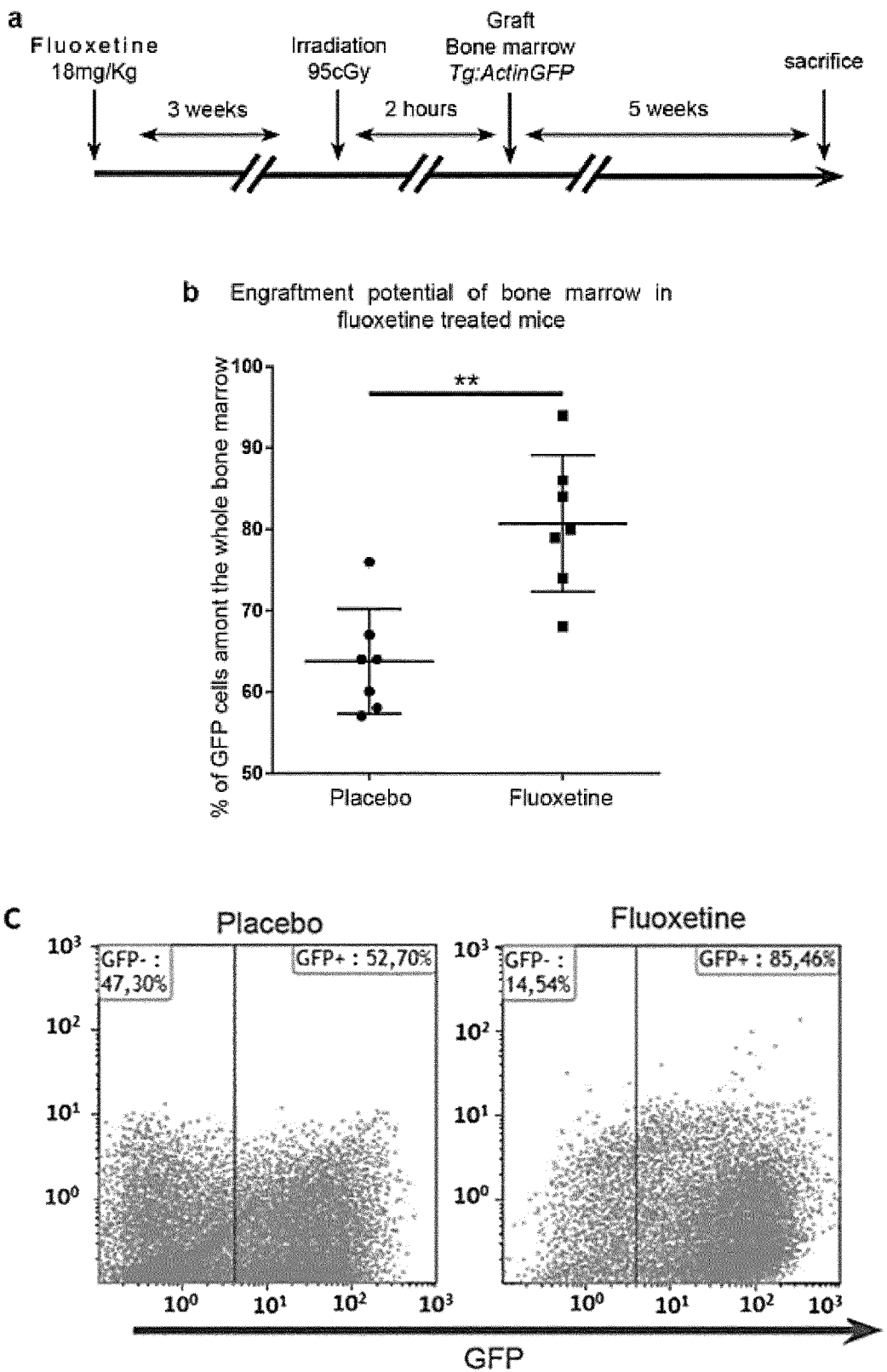
FIG. 2: Fluoxetine and vortioxetine increase the engraftment potential of hematopoietic stem cells. (a) Scheme of injection of fluoxetine. $Rag^{-/-}\gamma C^{-/-}$ mice were treated with fluoxetine for 3 weeks and irradiated at 95 cGy. 2 hours post irradiation mice were injected intra venously with fresh bone marrow coming from Tg:ActinGFP. 5 weeks post grafting the $Rag^{-/-}\gamma C^{-/-}$ bone marrow was flushed and analysed by cytometry. (b) Percentage of GFP+ cells among the $Rag^{-/-}\gamma C^{-/-}$ bone marrow 5 weeks after grafting. (c) Cytometry dot plot analysis of $Rag^{-/-}\gamma C^{-/-}$ bone marrow 5 weeks after grafting. (d) Scheme of injection of vortioxetine. $Rag^{-/-}\gamma C^{-/-}$ mice were treated with vortioxetine for 12 days and irradiated at 95 cGy. 2 hours post irradiation mice were injected intra venously with fresh bone marrow coming from Tg:ActinGFP. 5 weeks post grafting the $Rag^{-/-}\gamma C^{-/-}$ bone marrow was flushed and analysed by cytometry. (e) Percentage of GFP+ cells among the $Rag^{-/-}\gamma C^{-/-}$ bone marrow 5 weeks after grafting. (f) Scheme of injection of vortioxetine. In this condition the treatment with vortioxetine started the day of the irradiation. 2 hours post irradiation mice were injected intra venously with fresh bone marrow coming from Tg:ActinGFP. 5 weeks post grafting the $Rag^{-/-}\gamma C^{-/-}$ bone marrow was flushed and analysed by cytometry. (g) Representative histogram of the count and quantification of GFP+ cells by cytometry after vortioxetine treatment compared with placebo. Means±SD are displayed * $p<0.05$; ** $p<0.005$; ns: statistically not significant.
Figure 2:
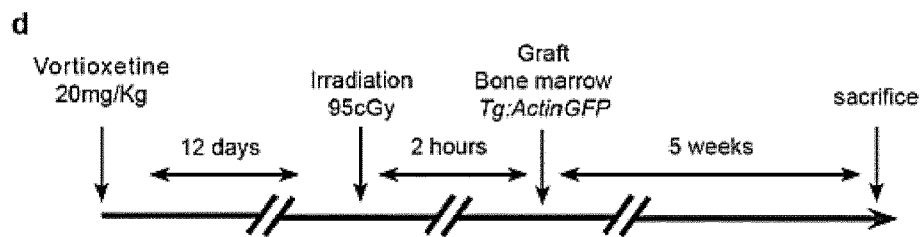
Figure 2:
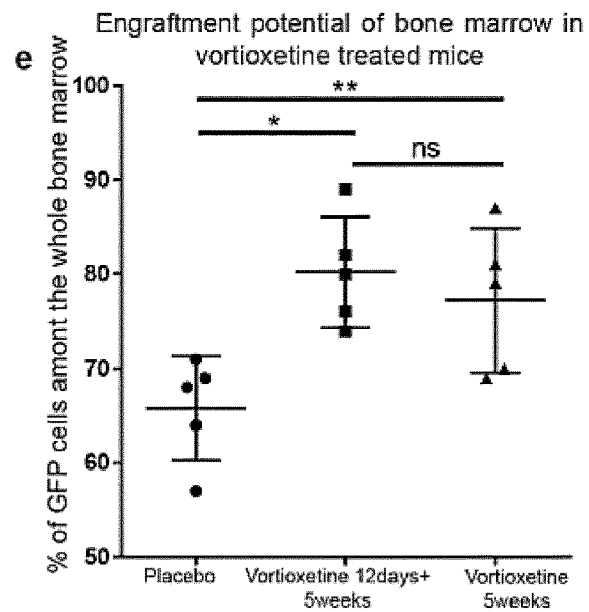
Figure 2:
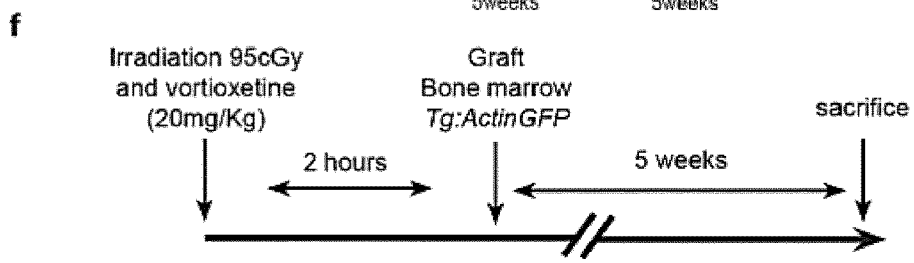
Figure 2:
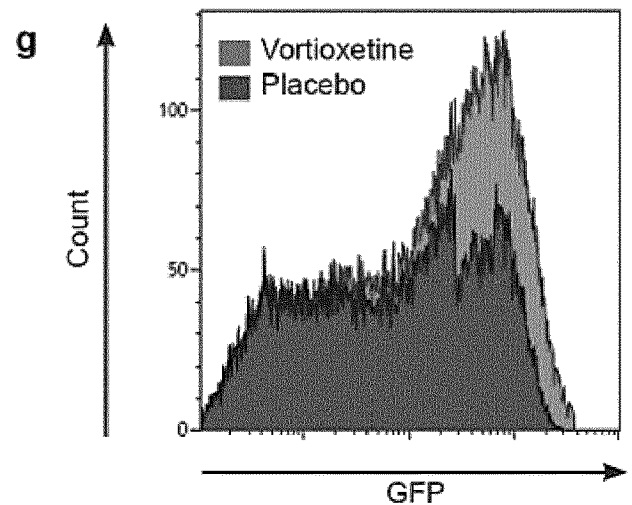

$Rag^{-/-}\gamma c^{-/-}$ mice were treated with fluoxetine per os at 18 mg/Kg for 6 weeks. After this period of time the mice were irradiated at 95 cGy and grafted with Tg:ActinGFP freshly isolated bone marrow cells (2 millions) (FIG. 2a). The number of GFP+ cells were investigated after 5 weeks in the bone marrow (the treatment was never discontinued). 63.7%±6.5 of GFP+ cells were detected in the placebo mice and 80.7%±8.4 GFP+ cells in the fluoxetine treated mice (p=0.0023, n=7, FIG. 2b,c). There was thus a 25% increase in engraftment efficiency in the fluoxetine treated animals.

To investigate the potential effect of vortioxetine on the engraftment potential, the same approach was used. The $Rag^{-/-}\gamma c^{-/-}$ were treated for 12 days by intra peritoneal injections at 20 mg/Kg. Twelve days after the beginning of the treatment, the mice were irradiated at 95 cGy and intravenously grafted with 2 million freshly isolated bone marrow cells from Tg:ActinGFP. 5 weeks after grafting the mice were sacrificed and bone marrow was flushed and analysed (FIG. 2d). The number of GFP+ cells was investigated after 5 weeks in the bone marrow (the treatment was never discontinued). 65.8%±5.5 cells were found in the placebo mice while 80.2%±5.8 cells were found in the vortioxetine treated animals (p=0.0079, n=5, FIG. 2e). There was thus a 21% increase in engraftment potential of bone marrow cells after vortioxetine treatment.

To further characterise the timing of vortioxetine beneficial effects, the previous experiment was repeated without 12 days of pre-treatment (FIG. 2e,f). $Rag^{-/-}\gamma c^{-/-}$ were irradiated and grafted 2 hours post irradiation fresh bone marrow from Tg:ActinGFP mice. The same placebo was used displaying 65.8%±5.5 of GFP+ cells and 77.2%7.6 GFP+ cells in the vortioxetine treated animals at the time of the irradiation (p=0.04, n=5, FIG. 2e,g). A similar increase in engraftment potential (17%) was observed when animals were not pre-treated.

2.3. Fluoxetine and Vortioxetine Treatment Stimulate the 5TH1B Receptor

Fluoxetine treatment was provided at 18 mg/Kg for 6 weeks to Rag$^{-/-}$γc$^{-/-}$ mice. The tibialis anterior (TA) was injured and 18 h post injury 10,000 satellite cells (SC) coming from Tg:Pax7nGFP:PLAP:MyHC2E3FLacZ triple transgenic mice were grafted to the Rag$^{-/-}$γc$^{-/-}$ mice pre-treated with fluoxetine. After 21 days, 25.7%±8.7 of the fibers observed were PLAP+ in the placebo group meaning that said fibers come from the graft, against 39%±6.6 PLAP+ in animals treated with fluoxetine (n=8 animals per condition) (FIG. 3).

Figure 3:
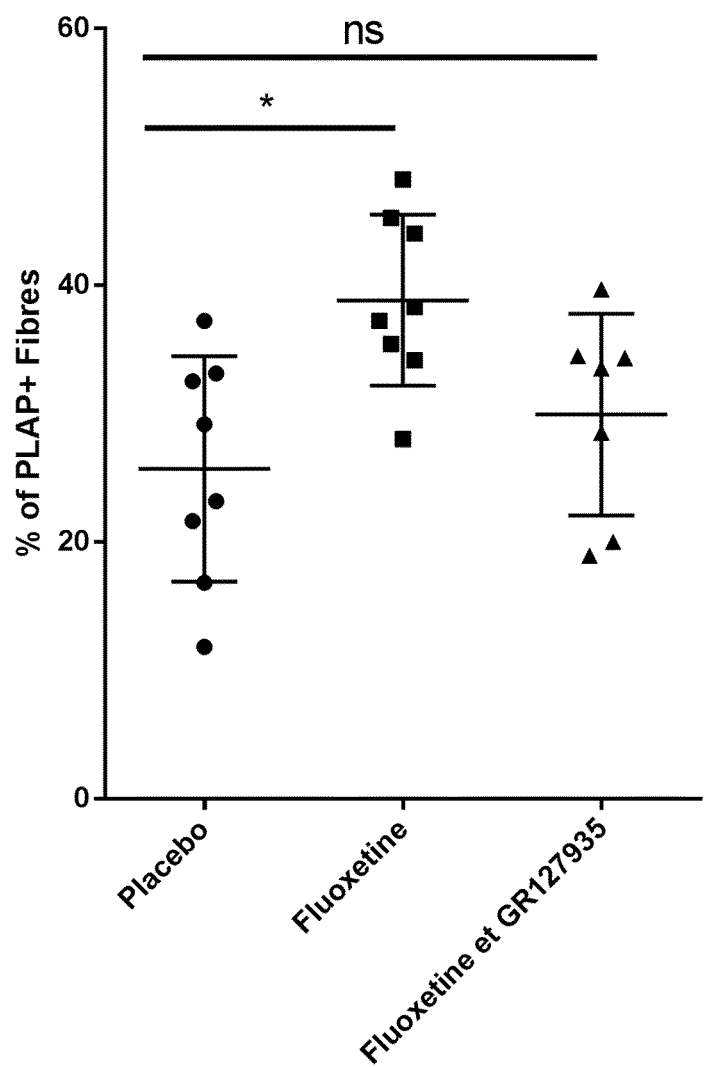
FIG. 3. Fluoxetine and vortioxetine treatment stimulate the 5TH1B receptor Scatter plot representing the percentage of PLAP+ fibers (coming from the graft) after grafting muscle stem cells in placebo, fluoxetine treated, and fluoxetine+GR127935 5HT1B inhibitor treated Rag2−/−γC−/− immunodeficient host mice.

When immunodeficient Rag$^{-/-}$γc$^{-/-}$ host animals were treated with fluoxetine at 18 mg/Kg but also with a 5HT1BR inhibitor (GR127935), 29.9%±7.8 of fibers were PLAP+, i.e. similar to the placebo situation (n=7 animals) (FIG. 3).

These data indicate that the inhibition of 5HT1BR in vivo is sufficient to lose the beneficial effect of fluoxetine, and that stimulation of 5HT1BR is the mode of action of fluoxetine for enhancement of the engraftment potential.

3. Discussion

The number of applications of cell or stem cell based therapies is limited to the clinics but the number of cell based clinical trials is currently growing (776 referenced world-wide, including 590 in the USA and 101 in Europe). Thus, having a drug capable of improving the engraftment potential of cell therapies (e.g. embryonic cells, adult cells, or stem cells) in order to better control diseases and the reconstitution of the tissue is key for a successful use of this emerging new type of medicine.

Here, the present results show that the use of two different drugs (fluoxetine and vortioxetine) that are known to stimulate the 5HT1B receptor, in two different paradigms (namely, the engraftment of muscle stem cells and the engraftment of bone marrow cells), is beneficial and that after grafting cells, the percentage or area of the tissue that was reconstituted from the donor cells was higher. It was further observed that the potential of vortioxetine in this respect was greater than the one of fluoxetine, due to the earlier onset of its beneficial effects on in vivo cell engraftment. After delivery of a 5HT1B inhibitor, it was observed that the effect of these drugs was obtained via the stimulation of the 5HT1B receptor.

These results are promising and can find direct applications in graft of bone marrow in leukaemia or graft of muscle stem cells in dystrophic patients, in order to improve said therapies.

Another important field of application comes from the mesenchymal stem cells (MSC) field. Indeed, safety and regulatory concerns surrounding allogeneic cell preparations make autologous and minimally manipulated cell therapies an attractive option for many regenerative, anti-inflammatory and autoimmune applications. MSCs have been shown to have interesting trophic properties (anti-scarring, anti-apoptotic, angiogenic, mitogenic, immuno-modulatory effects, anti-Microbial effects. So as a result, the MSCs are nowadays used in many studies and many clinical trials such as orthopaedics and spine therapies: fracture repair, osteonecrosis, spine fusion, cartilage repair, arthrisis; cardiovascular therapies: cardiac, vascular diseases; wounds and tissue repair: wounds and ulcer, burns, neural disorders: multiple sclerosis and amyotrophic lateral sclerosis, Parkinson's disease, stroke, spinal cord injury; autoimmune disorders: rheumatoid arthritis, Crohn's disease, lupus erythematosus, asthma; oncology leukaemia. One of the big advantages of those MSCs is the fact that they are not necessary immunogenic, they can be used in autograft but allograft has already proven to be also efficient. All those studies could benefit from the drugs that are under development by improving the engraftment and preparing the ground for better engraftability of the cells.

Other applications that are of main interest are cardiac tissue regenerative medicine that involves cardiomyocyte regeneration, neovascularization, and paracrine cytokines, which have anti-inflammatory, anti-apoptotic, and anti-remodelling effects. During the last decade, stem cells have become promising candidates for regenerative medicine not only because of their capacity of differentiation toward cardiomyocyte and vascular cell lineages but also their capacity for releasing such paracrine factors and their antiarrhythmic effects. Paracrine cytokines and chemokines play pivotal roles in stem cell-related cardiac repair mechanisms. All studies demonstrating a beneficial effect of stem cell therapy on myocardial infarction (MI) agreed to stress the importance of the cardioprotective effects of those cells.

REFERENCES

DePrimo S E, Stambrook P J, and Stringer J R (1996). *Transgenic Res.;* 5(6):459-66.

Farmaco, 1989, 44, from p. 683.

Fernandez C E, Achneck H E, Reichert W M, and Truskey G A (2014). *Curr Opin Chem Eng.;* 3:83-90.

Goumans M J, Maring J A, Smits A M (2014). *Heart;* 100(15):1153-7.

Jin H, Oksenberg D, Ashkenazi A, Peroutka S J, Duncan A M, Rozmahel R, Yang Y, Mengod G, Palacios J M, O'Dowd B F (1992). *J. Biol. Chem;* 267 (9): 5735-8.

Konofaos P, and Ver Halen J P (2013). *J Reconstr Microsurg.;* 29(3):149-64.

Kuroda N, Ohyama Y, Nakashima K, Nakashima K, and Akiyama S (1996). Chemical and Pharmaceutical Bulletin; 44(8): 1525-1529.

Li H, Malhotra D, Yeh C C, Tu R, Zhu B Q, Birger N, Wisneski A, Cha J, Karliner J S, Mann M J (2009). *Am Coil Surg.;* 208(4):607-13.

Li S, Sengupta D, and Chien S. (2013). *Rev Syst Biol Med.;* 6(1):61-76.

Lundberg M S (2013). *Circ Res.;* 112(8):1097-103.

Meng J, Bencze M, Asfahani R, Muntoni F, Morgan J E (2015). *Skelet. Muscle;* 5:11.

Mokrosz J L, Pietrasiewicz M, Duszynska B, and Cegla M (1992). *J. Med. Chem.;* 35 (13): 2369-2374.

Nakaya K, Tanaka T, Shirataki Y, Shiozaki H, Funabiki K, Shibata K, Matsui M. (2001). *Bulletin of the Chemical Society of Japan.;* 74(1): 173-177.

Neal R A, Jean A, Park H, Wu P B, Hsiao J, Engelmayr G C, Langer R, and Freed L E (2013). *Tissue engineering*; Part A (19): 5-6, 793-807.

Okabe M, Ikawa M, Kominami K, Nakanishi T, and Nishimune Y (1997). *FEBS Lett;* 407(3):313-9.

Perin E C, Dohmann H F, Borojevic R, Silva S A, Sousa A L, Mesquita C T, Rossi M I, Carvalho A C, Dutra H S, Dohmann H J, Silva G V, Belém L, Vivacqua R, Rangel F O, Esporcatte R, Geng Y J, Vaughn W K, Assad J A, Mesquita E T, Willerson J T (2003). *Circulation;* 107(18): 2294-302.

Rennert R C, Sorkin M, Garg R K, Gurtner G C (2012). *Regen Med.;* 7(6):833-50.

Rocheteau P, Gayraud-Morel B, Siegl-Cachedenier I, Blasco M A, and Tajbakhsh S (2012). *Cell;* 148(1-2):112-25.

Romanelli M N, Manetti D, Scapecchi S, Borea P A, Dei S, Bartolini A, Ghelardini C, Gualtieri F, Guandalini L, and Varani K (2001). *J Med Chem.;* 44(23):3946-55.

Sanchez F M, Cuadra G I, Nielsen S J, Tanner A, Berges B K (2013). *Methods Mol Biol;* 1031:19-26.

Schmuck K, Ullmer C, Engels P, Lübbert H (1994). *FEBS Lett;* 342(1):85-90.

Zimmermann W H, and Eschenhagen T. (2003). *Heart Fail Rev.;* 8(3):259-69.

The invention claimed is:

1. A method for enhancing the in vivo engraftment potential of a cell, tissue or organ graft, comprising at least the step of in vitro and/or ex vivo contacting an isolated cell, tissue or organ graft with at least one direct 5-hydroxytryptamine 1B receptor (5-HT1 BR)-stimulating agent.

2. The method of claim 1, wherein the direct 5-HT1 BR-stimulating agent is a selective or partially selective 5-HT1 BR agonist.

3. The method of claim 1, wherein the agent is vortioxetine.

4. The method according to claim 1, wherein the agent is modified to comprise at least one positively charged chemical moiety.

5. The method of claim 4, wherein the agent is a positively charged vortioxetine selected from the group consisting of salts of vortioxetine, vortioxetine coupled to a positively charged amino acid, pyrrolidinium-vortioxetine, pyperazinium-vortioxetine, dimethylammonium-vortioxetine, sulfonium-vortioxetine, N-oxide-vortioxetine, sulfoxide-vortioxetine, and phosphonium-vortioxetine.

6. The method of claim 4, wherein the agent is histidine-vortioxetine or pyrrolidinium-vortioxetine.

7. The method according to claim 4, wherein said positively charged chemical moiety is a quaternary ammonium group or a tertiary sulfonium group.

8. The method according to claim 7, wherein said quaternary ammonium group has the formula (I)

$$-(NR_1R_2R_3)^+Z^- \qquad (I)$$

wherein

Z is an organic or inorganic anion; and $R_1$, $R_2$, and $R_3$ are each independently selected from the group consisting of alkyl, aryl and cycloalkyl;

or said tertiary sulfonium group has the formula (II)

$$-(SR_4R_5)^+Z^- \qquad (II)$$

wherein

Z is an organic or inorganic anion; and $R_4$ and $R_5$ are each independently selected from the group consisting of alkyl, aryl and cycloalkyl.

9. The method according to claim 5, wherein said positively charged amino acid is selected from the group consisting of histidine, arginine and lysine.

10. The method according to claim 1, wherein the agent is ergotamine or a triptan.

11. The method of claim 10, wherein the triptan is selected from the group consisting of rizatriptan, zolmitriptan, eletriptan, almotriptan, frovatriptan, naratriptan avitriptan, and donitriptan.

* * * * *